(12) United States Patent
Chen et al.

(10) Patent No.: US 9,907,908 B2
(45) Date of Patent: Mar. 6, 2018

(54) NON-INVASIVE RADIO FREQUENCY MEDICAL FLUID LEVEL AND VOLUME DETECTION SYSTEM AND METHOD

(75) Inventors: Ye Chen, Buffalo Grove, IL (US); Yuanpang Samuel Ding, Libertyville, IL (US); Matthew Muller, Lindenhurst, IL (US); Gert Najdeni, Chicago, IL (US); Joel Titus, Lake Zurich, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1393 days.

(21) Appl. No.: 13/253,691

(22) Filed: Oct. 5, 2011

(65) Prior Publication Data

US 2012/0232471 A1 Sep. 13, 2012

Related U.S. Application Data

(60) Provisional application No. 61/450,452, filed on Mar. 8, 2011, provisional application No. 61/451,725, filed on Mar. 11, 2011.

(51) Int. Cl.
*A61M 5/168* (2006.01)
*A61M 1/14* (2006.01)
(Continued)

(52) U.S. Cl.
CPC ............ *A61M 5/1684* (2013.01); *A61M 1/14* (2013.01); *A61M 1/1605* (2014.02);
(Continued)

(58) Field of Classification Search
CPC ........ A61M 5/1684; A61M 2205/3317; A61M 2205/3379; A61M 2205/3389;
(Continued)

(56) References Cited

U.S. PATENT DOCUMENTS 3,508,656 A 4/1968 Serfass et al.
3,729,729 A 4/1973 Geller et al.
(Continued)

FOREIGN PATENT DOCUMENTS

AU 2010/249145 12/2010
CA 2607995 11/2006
(Continued)

OTHER PUBLICATIONS

International Search Report for Application No. PCT/US2012/027478 dated Sep. 28, 2012.
(Continued)

*Primary Examiner* — Shefali Patel
(74) *Attorney, Agent, or Firm* — K&L Gates LLP

(57) ABSTRACT

A medical fluid system includes a medical fluid pump; a container holding a fluid to be pumped by the medical fluid pump, the fluid at a first time having a first conductivity, the fluid at a second time having a second conductivity; and a radio frequency level sensor positioned in operable relation with the container, the radio frequency level sensor (i) configured to provide an output indicative of a level of the fluid in the container based upon sensing an impedance and (ii) connected to tuning circuitry that minimizes a reactance of the impedance such that the output is at least substantially independent of whether the fluid has the first conductivity or the second conductivity. The medical fluid system can determine the level of the fluid by measuring a resistance, the impedance, or a phase shift seen by the sensor.

26 Claims, 15 Drawing Sheets

(51) Int. Cl.
    *A61M 1/16*           (2006.01)
    *A61M 5/14*           (2006.01)
    *A61M 5/142*          (2006.01)
    *G01F 23/26*          (2006.01)
    *G01F 23/284*        (2006.01)
    *G01F 22/00*          (2006.01)
    *A61M 1/28*           (2006.01)

(52) U.S. Cl.
    CPC ............ *A61M 1/1668* (2014.02); *A61M 1/28* (2013.01); *A61M 1/287* (2013.01); *A61M 5/14* (2013.01); *A61M 5/142* (2013.01); *A61M 5/1407* (2013.01); *A61M 5/1409* (2013.01); *G01F 22/00* (2013.01); *G01F 23/26* (2013.01); *G01F 23/284* (2013.01); *A61M 1/16* (2013.01); *A61M 1/1607* (2014.02); *A61M 2205/3317* (2013.01); *A61M 2205/3379* (2013.01); *A61M 2205/3389* (2013.01); *A61M 2205/52* (2013.01); *G01F 23/263* (2013.01)

(58) Field of Classification Search
    CPC ........ A61M 1/14; A61M 1/16; A61M 1/1605; A61M 1/1607; A61M 1/1609; A61M 1/1668; A61M 1/28; A61M 1/287; A61M 5/14; A61M 5/1407; A61M 5/1409; A61M 5/142; A61M 2205/3327; A61M 2205/3382; A61M 2205/3386; G01F 22/00; G01F 23/26; G01F 23/261; G01F 23/263; G01F 23/265; G01F 23/266; G01F 23/28; G01F 23/282; G01F 23/284; G01F 23/2845

See application file for complete search history.

(56) References Cited

U.S. PATENT DOCUMENTS

| | | | |
|---|---|---|---|
| 4,002,996 A | 1/1977 | Klebanoff et al. | |
| 4,099,167 A | 7/1978 | Pomerantz et al. | |
| 4,169,543 A | 10/1979 | Hall | |
| 4,213,337 A | 7/1980 | Langdon | |
| 4,222,267 A | 9/1980 | Aldrich | |
| 4,359,902 A | 11/1982 | Lawless | |
| 4,418,569 A | 12/1983 | Kuhnel | |
| 4,472,968 A | 9/1984 | Coates | |
| 4,676,101 A | 6/1987 | Baughman | |
| 4,729,245 A | 3/1988 | Hansman, Jr. | |
| 4,749,988 A | 6/1988 | Berman et al. | |
| 4,765,186 A | 8/1988 | Dieulesaint et al. | |
| 4,800,755 A | 1/1989 | Fathauer et al. | |
| 4,833,918 A | 5/1989 | Jean et al. | |
| 4,896,535 A | 1/1990 | Duckart et al. | |
| 5,088,325 A | 2/1992 | Eichberger et al. | |
| 5,365,178 A | 11/1994 | Van Der Pol | |
| 5,400,651 A | 3/1995 | Welch | |
| 5,406,842 A | 4/1995 | Locke | |
| 5,609,059 A | 3/1997 | McEwan | |
| 5,689,265 A | 11/1997 | Otto et al. | |
| 5,743,134 A | 4/1998 | Dreyer | |
| 5,757,197 A | 5/1998 | O'Neill | |
| 5,811,677 A | 9/1998 | Cournanc | |
| 5,832,772 A | 11/1998 | McEwan | |
| 5,841,028 A * | 11/1998 | Bray ................ | G01F 23/2845 137/392 |
| 5,877,663 A | 3/1999 | Palen et al. | |
| 5,880,698 A | 3/1999 | Burger | |
| 5,996,407 A | 12/1999 | Hewitt | |
| 6,053,041 A | 4/2000 | Sinha | |
| 6,085,589 A | 6/2000 | Cruickshank | |
| 6,192,751 B1 | 2/2001 | Stein et al. | |
| 6,192,752 B1 | 2/2001 | Blaine | |
| 6,269,340 B1 | 7/2001 | Ford et al. | |
| 6,293,142 B1 | 9/2001 | Pchelnikov et al. | |
| 6,489,896 B1 | 12/2002 | Platt et al. | |
| 6,490,920 B1 | 12/2002 | Netzer | |
| 6,515,487 B1 | 2/2003 | Dawson et al. | |
| 6,546,795 B1 | 4/2003 | Dietz | |
| 6,606,904 B2 | 4/2003 | Willer et al. | |
| 6,614,391 B1 | 9/2003 | Burger et al. | |
| 6,629,449 B1 | 10/2003 | Kline-Schoder et al. | |
| 6,631,639 B1 | 10/2003 | Dam et al. | |
| 6,644,119 B1 | 11/2003 | Sinha | |
| 6,650,280 B2 | 11/2003 | Arndt et al. | |
| 6,675,647 B2 | 1/2004 | Marioni | |
| 6,708,569 B2 | 3/2004 | Budmiger | |
| 6,726,774 B2 | 4/2004 | Tzeng et al. | |
| 6,845,663 B2 | 1/2005 | Lopatin et al. | |
| 6,899,560 B2 | 5/2005 | Katayama | |
| 6,912,904 B2 | 7/2005 | Storm, Jr. et al. | |
| 6,959,598 B2 | 11/2005 | Peterson et al. | |
| 6,959,599 B2 | 11/2005 | Feldstein et al. | |
| 6,962,078 B2 | 11/2005 | Angel et al. | |
| 7,010,962 B2 | 3/2006 | Sinha | |
| 7,013,703 B2 | 3/2006 | Derek et al. | |
| 7,084,646 B2 | 8/2006 | Gruebler et al. | |
| 7,096,710 B2 | 8/2006 | Preckel et al. | |
| 7,107,836 B2 | 9/2006 | Brookner | |
| 7,114,390 B2 | 10/2006 | Lizon et al. | |
| 7,145,349 B1 | 12/2006 | Cramer et al. | |
| 7,162,374 B2 | 1/2007 | Burkhardt | |
| 7,232,430 B2 | 6/2007 | Carlisle et al. | |
| 7,258,005 B2 | 8/2007 | Nyce | |
| 7,340,951 B2 | 3/2008 | Nyce et al. | |
| 7,403,862 B2 | 7/2008 | Budmiger et al. | |
| 7,407,154 B2 | 8/2008 | Sakakibara et al. | |
| 7,421,895 B1 | 9/2008 | Caldwell | |
| 7,415,366 B2 | 10/2008 | Florenz et al. | |
| 7,456,752 B2 * | 11/2008 | Oberle ................ | G01N 27/023 340/539.26 |
| 7,479,391 B2 | 1/2009 | Bjornson et al. | |
| 7,482,818 B2 | 1/2009 | Greenwald et al. | |
| 7,497,957 B2 | 3/2009 | Frank | |
| 7,509,856 B1 | 3/2009 | Winkens et al. | |
| 7,573,009 B2 | 8/2009 | Lunneborg et al. | |
| 7,614,302 B2 | 11/2009 | DiFoggio et al. | |
| 7,621,181 B2 | 11/2009 | Cammarata et al. | |
| 7,661,293 B2 | 2/2010 | Dam | |
| 7,695,448 B2 | 4/2010 | Cassidy et al. | |
| 7,749,393 B2 | 7/2010 | Brugger et al. | |
| 7,799,574 B2 | 9/2010 | Saegusa | |
| 7,805,261 B2 | 9/2010 | Bell et al. | |
| 7,814,786 B2 | 10/2010 | Woodard | |
| 7,814,788 B2 | 10/2010 | Halaka et al. | |
| 7,814,789 B2 | 10/2010 | Schroth | |
| 7,823,446 B2 | 11/2010 | Nilsson et al. | |
| 7,861,600 B2 | 1/2011 | Mayer et al. | |
| 7,865,317 B2 | 1/2011 | Begin | |
| 7,891,243 B2 | 2/2011 | Winkens | |
| 7,895,890 B2 | 3/2011 | Van Ee | |
| 7,926,341 B2 | 4/2011 | Boudaoud et al. | |
| RE42,386 E | 5/2011 | Wanie | |
| 7,938,180 B2 | 5/2011 | Levy | |
| 7,987,722 B2 | 8/2011 | Hills | |
| 2002/0104370 A1 | 8/2002 | Steger et al. | |
| 2004/0119637 A1 | 6/2004 | Angal et al. | |
| 2006/0020208 A1 | 1/2006 | Egozi | |
| 2008/0103445 A1 | 5/2008 | Blaine et al. | |
| 2008/0105048 A1 | 5/2008 | Nilsson et al. | |
| 2009/0008331 A1 | 1/2009 | Wilt et al. | |
| 2009/0075129 A1 | 3/2009 | Sparks et al. | |
| 2009/0120203 A1 | 5/2009 | Schrag et al. | |
| 2009/0205426 A1 | 8/2009 | Balschat et al. | |
| 2009/0235738 A1 | 9/2009 | Uhov | |
| 2009/0275855 A1 * | 11/2009 | Zielinski ................ | A61B 5/053 600/547 |
| 2010/0066356 A1 | 3/2010 | Nieuwenhuis et al. | |
| 2010/0125245 A1 | 5/2010 | Geipel | |
| 2010/0126268 A1 | 5/2010 | Baily et al. | |
| 2010/0133189 A1 | 6/2010 | Maierhofer et al. | |
| 2010/0137778 A1 | 6/2010 | Kunjan et al. | |
| 2010/0145175 A1 | 6/2010 | Soldo et al. | |
| 2010/0164514 A1 | 7/2010 | Brandt et al. | |

(56) References Cited

U.S. PATENT DOCUMENTS

| | | | |
|---|---|---|---|
| 2010/0168624 A1 | 7/2010 | Sliwa | |
| 2010/0295565 A1 | 11/2010 | Drack | |
| 2010/0312174 A1* | 12/2010 | Hoffman | A61M 1/1696 604/29 |
| 2010/0313654 A1 | 12/2010 | Malinovskiy et al. | |
| 2010/0326282 A1 | 12/2010 | Carbonini et al. | |
| 2011/0166812 A1 | 7/2011 | Potyrailo et al. | |

FOREIGN PATENT DOCUMENTS

| | | |
|---|---|---|
| DE | 102006032602 | 1/2008 |
| DE | 19935743 | 2/2011 |
| EP | 102102 | 3/1984 |
| EP | 0261860 | 9/1987 |
| EP | 534654 | 3/1993 |
| FR | 2763682 | 11/1998 |
| JP | 61223618 | 10/1986 |
| JP | 63-158423 | 7/1987 |
| JP | 63259420 | 10/1988 |
| JP | H01254815 | 10/1989 |
| JP | 02150726 | 6/1990 |
| JP | 04-168325 | 6/1992 |
| JP | 06194212 | 7/1994 |
| JP | 2001-009028 | 1/2001 |
| WO | 88/10412 | 12/1988 |
| WO | 1996/023202 | 8/1996 |
| WO | 1999/10713 | 3/1999 |
| WO | 2001/020273 | 3/2001 |
| WO | 2004/005959 | 1/2004 |
| WO | 2006/063929 | 6/2006 |
| WO | 2006/097546 | 9/2006 |
| WO | 2006/122173 | 11/2006 |
| WO | 2007/062714 | 6/2007 |
| WO | 2007/121398 | 10/2007 |
| WO | 2007/139574 | 12/2007 |
| WO | 2009/094183 | 7/2009 |
| WO | 2010/063026 | 6/2010 |
| WO | 2011/095573 | 8/2011 |

OTHER PUBLICATIONS

Written Opinion for Application No. PCT/US2012/027476 dated Nov. 22, 2012.
First Action Interview Pilot Program Pre-Interview Communication dated Nov. 8, 2013 for U.S. Appl. No. 13/253,705.
Applicant-Initiated Interview Summary and First Action Interview Office Action Summary dated Jan. 2, 2014 for U.S. Appl. No. 13/253,705.
Japanese Office Action dated Dec. 1, 2015, for corresponding Japanese Appln. No. 2013-557768 (20 pages).
Japanese Office Action dated Dec. 1, 2015, for corresponding Japanese Appln. No. 2013-557769 (12 pages).
International Preliminary Report on Patentability for International Application No. PCT/US2012/027476 dated May 16, 2013.
Written Opinion of the International Preliminary Examining Authority for International Application No. PCT/US2012/027478 dated May 17, 2013.
Manns et al., The acu-menTM: A new device for continuous renal replacement therapy in acute renal failure, Kidney International, 1998, pp. 268-274, vol. 54.
International Search Report and Written Opinion for Application No. PCT/US2012/027476 dated Jul. 11, 2012.
Notification of Transmittal of the International Search Report and the Written Opinion of the International Searching Authority, or the Declaration for Application No. PCT/US2012/027478 dated Sep. 28, 2012.
International Preliminary Report on Patentability for PCT/US2012/027478 dated Aug. 28, 2013.
Essentials of RF and Microwave Grounding, Eric Holzman, 2006, pp. 60-61.
Japanese Office Action dated May 16, 2016, for corresponding Japanese Appln. No. 2013-557768 (6 pages).
Slot-Line—An Alternative Transmission Medium for Integrated Circuits by S. B. Cohn, Consultant, Stanford Research Institute, 1996 pp. 104-109.
Microstrip Lines and Slotlines, Second Edition, by K.C. Gupta et al., 1996 Artech House, Inc., pp. 269-340.

* cited by examiner

Impedance changes based on water levels

NON-INVASIVE RADIO FREQUENCY MEDICAL FLUID LEVEL AND VOLUME DETECTION SYSTEM AND METHOD

This application claims priority to U.S. Patent Application Ser. No. 61/450,452, entitled "NON-INVASIVE RADIO FREQUENCY LIQUID LEVEL AND VOLUME DETECTION SYSTEM," filed Mar. 8, 2011, and U.S. Patent Application Ser. No. 61/451,725, entitled "NON-INVASIVE RADIO FREQUENCY LIQUID LEVEL AND VOLUME DETECTION SYSTEM USING PHASE SHIFT," filed Mar. 11, 2011.

BACKGROUND

The present disclosure relates to sensing the level of a medical fluid in a container.

Knowing a volume or level of a medical fluid in a container is important in many medical fluid applications. For example, it may be important to know when a medical fluid supply is running low, so that a new source of fluid can be installed or opened. In a reusable container, it may be important to know the liquid level to ensure that the container is not overfilled but has enough supply for whatever use is necessary.

Certain existing medical device sensors require that an associated pump or moving part be stopped before a fluid level can be sensed accurately. Stopping the therapy to take a measurement results in a point in time system as opposed to a true real time system. Stopping therapy also lengthens overall therapy time.

Other existing sensors use a capacitive probe or capacitive element that measures a distance between the probe and the fluid. Capacitive sensors rely on the conductivity of the fluid and thus may not be desirable in medical applications in which the conductivity of a measured fluid changes during therapy. For example, in dialysis applications, the conductivity of dialysis fluid may fluctuate as the fluid is regularly modified, refreshed, and rejuvenated. Dialysis and other medical fluid applications may accordingly provide a container that holds different fluids having different conductivities at different times. In such applications, it may be advantageous to have a level sensor that is at least substantially independent of or unaffected by fluid conductivity.

Another class of existing sensors relies on radiating a signal from a transmitter to a receiver and measuring the attenuation of the radiated signal to determine whether fluid exists at various points inside a container. Radiation in medical applications is undesirable because it can interfere with nearby equipment and may be harmful to the patient.

Other existing sensors rely on invasive probes that must be in contact with the measured fluid or need to be located inside the container where the measured fluid resides. The probes present sterility and disinfection issues. Residue can build up on the probe, requiring additional maintenance and cleaning. Probe systems can also make swapping or changing fluid containers cumbersome. Opening a new container to insert a probe requires the container to be openable and presents further sterilizing issues. It would therefore also be advantageous to have a non-invasive sensor that does not require physical contact with the fluid and does not need to be placed inside the container.

A need accordingly exists for an improved medical tank level sensor.

SUMMARY

The present system and method involve a medical fluid application in which a level or volume of a medical fluid in a container is sensed and known. The medical fluid system in one embodiment is a renal failure therapy system, such as a hemodialysis ("HD"), hemofiltration ("HF"), hemodiafiltration ("HDF") or continuous renal replacement ("CRRT") system. The dialysis system is alternatively a peritoneal dialysis ("PD") system. The dialysis system may be an online system, in which dialysis fluid or dialysate is made during treatment. The dialysis system may alternatively be a batch system, in which the dialysate is made and stored for one or more treatment. The dialysis system may further alternatively be a bagged system in which the dialysate is premade before therapy.

In any of the above renal failure or dialysis systems, it is contemplated that there is a container, e.g., rigid tank or bag, in which it is desirable to know the level or volume, and in which the container at different times holds fluids having differing conductivities. For example, the online dialysis system can have the ability to pump purified water or mixed dialysate. The water can be pumped to prime, flush and/or disinfect the dialysis system. The mixed dialysis fluid or dialysate is pumped during therapy. A fluid holding tank is provided to hold a ready supply of either purified water or dialysate, so that if needed, an additional volume of fluid (water or dialysate) can be delivered to an associated dialyzer or hemofilter or elsewhere as needed. The level or volume detection system and method of the present disclosure is coupled operably to the tank as discussed in detail below to know, in real time, the level or volume of purified water or dialysate in the holding tank. The measurement is accurate regardless of fluid conductivity, for example, regardless of whether water, dialysate, or some intermediate version thereof, is present in the container.

In another dialysis example, a batch supply of dialysate is made at the site of the dialysis therapy. For example, a batch supply of twenty to one-hundred liters is made in a batch container for one or more therapy. The batch container can be a container having a pre-supplied amount of concentrate to make a predefined volume of dialysate. Purified water is then added to make the specified amount of dialysate. As water is added, the conductivity of the mixture changes—that is, lessens—as the pre-supplied concentrate is diluted to the desired level. The level or volume detection system and method of the present disclosure is coupled operably with the batch container to know, as the batch container is being filled, the level or volume of the water that has been added to the container. The sensing system and method is used to detect when the filling of the purified water and the preparation of the dialysate has been completed. It is thereafter used to know how much of the mixed dialysate has been used during a single therapy or over multiple therapies.

In a further dialysis example, bagged dialysis fluid is provided, e.g., for PD. First and second bagged dialysates can be provided having first and second different dextrose levels, and thus different conductivities. The first and second dialysates can be administered sequentially or be mixed in a container to form a blended dialysate having a dextrose level tailored for the patient. The container may also be used as a container for heating and/or weighing of the dialysis fluids. The present level and volume detection system and method is provided to know how much dialysate is present (during filling and draining to the patient) in the mixing/heating container regardless of whether only the first dialysate is pumped to the container, only the second dialysate is pumped to the container, or a blend of the first and second dialysates is pumped to the container.

In another PD implementation, bagged dialysis fluid components are provided and are mixed in a container to form an overall mixed dialysate that is delivered to the patient. The present level and volume detection system and method is provided to know how much of each component is added to the container to achieve a desired mix ratio. The system and method can then be used to know how much of the mixed dialysate remains in the tank during the course of therapy. The tank as above can be further used to heat and/or weigh the mixed dialysate.

The present system and method are not limited to renal failure therapies and can be used with any type of medical fluid delivery. In a drug infusion example, it the drug infusion can include multiple liquid or liquefied drugs that are delivered to the patient sequentially or in a combined manner. In another example, supplies of multiple constituents of a drug may be blended at the time of use, e.g., if the mixed drug is unstable if stored over a period of time. The different drugs and constituents can have different conductivities. A container is provided in use with the level or volume sensing system and method of the present disclosure, such that the volume or level of any drug, any constituent, or any combination of drug or constituent can be sensed, regardless of conductivity, and regardless of whether the conductivity is static or changing.

In one embodiment, the tank level or volume sensing system includes an electrically insulating substrate onto which a pair of radio frequency ("RF") probes or electrodes is applied. The substrate can for example be made of an FR-4 or printed circuit board material, a plastic material, a glass or ceramic material, a polyimide material, or be a combination of any of the above. The electrodes, which can be copper, aluminum, nickel, lead, tin, silver, gold, alloys thereof, and combinations thereof, are plated, adhered, soldered, sputtered, mechanically fixed to the insulating substrate, or done so using a combination of these techniques.

The electrodes are sized and positioned relative to each other so as to be able to transmit a radio frequency signal, one electrode being the signal or emitting electrode, the other electrode being the receiving or ground electrode. The electrodes extend along the substrate, e.g., vertically, a distance corresponding to a full level of the tank or container. The electrodes can for example be about 12 mm (47 inch) wide and be spaced apart from each other about 2 mm (08 inch) to about 8 mm (31 inch), although other distances may be obtainable. The thickness of the electrodes can be a standard application thickness for whatever application process is used for applying the electrodes to the substrate, for example, about 100 micrometers. The substrate is fixed close to the tank or container, for example, about 2 mm (0.08 inch) from the container. As described below, the dimensions of the sensors may be optimized to improve system reliability.

In an alternative embodiment, the electrodes are applied directly to the outside of the tank or container. Here, the additional substrate is not needed. In either case it should be appreciated the electrodes do not contact the medical fluid and therefore cannot contaminate the fluid.

The electronic circuitry can be provided in whole or in part on the substrate or on a separate circuit board located with the other controllers and circuit boards of the medical fluid machine, for example, in a safe area of the machine for housing electronics. The electronics can include, for example, an oscillator that oscillates or generates a radio frequency signal. The signal can be a low power signal, e.g., on the order of −10 dBm (the power ratio in decibels of the measured power referenced to one milliwatt). The RF signal is amplified and then sent to the signal or emitting probe of the sensor. The signal may optionally be matched before it is sent to the signal probe of the sensor. The receiving or ground probe of the sensor picks up the transmitted RF signal and then returns the signal to ground.

As the signal travels from one probe to the other, an electric field ("EF") is generated, which travels from the positively charged probe to the negatively charged probe. An RF wave propagates between the two metal electrodes along the side of the tank and perpendicular to the direction of the electric field. The impedance that the RF transmission sees or is subjected to when traveling from the signal electrode to the receiving electrode changes based upon the amount of medical fluid through which the electric field has to pass. The RF wave passes through an unchanging medium, such as air, on the side of the sensor substrate facing away from the tank. On the side of the sensor substrate facing the tank, however, the RF wave passes through a changing combination of air and medical fluid. The more full the tank or container, the more liquid the wave sees along its transmission path.

As described in additional detail below, the two strips of conductive material fixed to the side of the tank can be operated as a transmission line. In one model of the equivalent transmission line, the water in the tank represents the load of the transmission line. As the water level changes, the overall load seen by the transmission line also changes, changing the overall impedance. Thus, measuring a change in impedance allows determining the water level in the tank.

In one embodiment the system senses the overall impedance seen by the transmission line. The sensed impedance is governed by the equation:

$$Z_o = \sqrt{\frac{\mu o}{\varepsilon}} F(g),$$

where F(g) is a function of the geometry of the electrodes, $\mu_o$ is the permeability of free space, and $\in$ is an equivalent dielectric of the overall medium through which the RF signal must pass when traveling along the transmission line. The equivalent dielectric $\in$ can be characterized as follows:

$$\varepsilon \approx \frac{\varepsilon o + \varepsilon d}{2},$$

where $\in_o$ is the dielectric constant of free space and $\in_d$ is the dielectric constant of water, dialysate, drug, medicament or other water-based medical fluid. When the liquid level in the tank or container changes $\in$, the equivalent dielectric, changes accordingly, affecting the sensed impedance $Z_o$ according to the equation above. Applicants have successfully tested the tank level or volume sensing system of this disclosure. Data for the tests is illustrated below.

As is known to one of skill in the art, the impedance is made up of the resistance and the phase as shown by the following equation:

$Z=R+jX$, where

Z is the overall impedance,

R is the resistance, and

X is the phase seen by the transmission line. Depending on circuitry used with the sensor, the water level or volume in the tank can be determined based not only on the impedance, but also on the resistance or the phase seen by the system.

In one embodiment the system senses the resistance seen by the transmission line. The electronics in this embodiment includes a resistance sensing circuit that measures the resistance along the electrical line leading from the amplifier to the signal electrode (i.e., measures the real part of the sensor's input impedance as opposed to its reactance). An output of the resistance sensing circuit is converted to a duty cycle, amplified, digitized and then sent to a microprocessor and associated memory to be analyzed and converted into a tank level value or a tank volume value. The microprocessor and associated memory, like the other electronics of the tank level or volume sensing system, can be located locally at the sensor substrate or remotely with the other electronics of the medical machine. The same microprocessor and associated memory in one embodiment controls the RF oscillator and receives the digitized duty cycle resistance output.

As discussed herein, the RF sensing system may include tuning electronics, including for example capacitors and inductors, that are sized to minimize, as much as possible, the output of the impedance that would be affected by changes in conductivity. The sensor output may be shifted to minimize or zero out the reactive or imaginary part of the impedance, so that the output consists largely of the real or resistive part of the impedance. By doing so, the sensing system is advantageously unaffected by the conductivity of the medical fluid for certain frequencies, allowing different fluids to be delivered to the tank or container at different times, and allowing each fluid to be sensed accurately and repeatably.

In another embodiment, the sensing system of the present disclosure looks instead to the electrical phase shift that also accompanies the change in impedance due to the overall change in the dielectric. In describing this embodiment, it is important to understand the difference in physical length of the transmission lines or electrodes and an "electrical length" associated with the changing dielectric. The electrical length is proportional to the physical length of the transmission line or electrodes. In particular, the electrical length can be expressed as a function of the physical length L of the transmission line, as follows:

$$\text{electrical length} = \in * \beta_0 * L, \text{ where}$$

$\in$ is the overall dielectric constant, $\beta_0$ is the wave number in free space, and is a constant, and L is again the physical length of the transmission line or sensor, and is a constant.

Overall dielectric constant $\in$ as shown in the equation above is a function of $\in_o$, the dielectric constant of free space, and $\in_d$, the dielectric constant of water, dialysate, drug, medicament or other water-based medical fluid. When the liquid level in the tank or container changes, the electrical length also changes according to the equation:

$$\text{change in electrical length} = 2\in_1 \beta_0 L - 2\in_2 \beta_0 L, \text{ where}$$

$\in_1$ is the overall equivalent dielectric constant at liquid level 1, and $\in_2$ is the overall equivalent dielectric constant at liquid level 2.

The tank and electrodes used for the resistance sensing embodiment, impedance sensing embodiment or phase shift embodiment can be the exact same structures. The circuitry for the resistance, impedance, or phase shift embodiments, which can be implemented and located in any of the manners described herein, will be different. In one embodiment, the phase shift circuitry described in detail below uses a frequency mixer that outputs a direct current ("DC") signal indicative of phase shift.

The phase shift due to changing dielectric is not affected by fluid conductivity. Unlike the resistance system or impedance system, which may need to be tuned so as not to be affected by fluid conductivity, the phase shift system is inherently unaffected by fluid conductivity. Thus, tuning circuitry is not needed with the phase shift system, which is advantageous.

Based on the foregoing and following description, it should be appreciated that it is an advantage of the present disclosure to provide a tank or container level or volume sensing system that is robust.

It is another advantage of the present disclosure to provide a tank or container level or volume sensing system that is relatively inexpensive.

It is a further advantage of the present disclosure to provide a tank or container level or volume sensing system that is accurate and repeatable.

It is yet another advantage of the present disclosure to provide a tank or container level or volume sensing system that provides information in real time.

It is yet a further advantage of the present disclosure to provide a tank or container level or volume sensing system that is non-invasive, allows for a hermetically sealed container, and does not require direct sensing contact with the sensed fluid.

Moreover, it is an advantage of the present disclosure to provide a tank or container level or volume sensing system that is inherently unaffected by fluid conductivity, such that different medical fluids or different components thereof can be sensed at different times.

It is still a further advantage of the present disclosure to provide a tank or container level or volume sensing system that is compatible with medical fluid mixing, medical fluid preparation, and medical fluid delivery.

Additional features and advantages are described herein, and will be apparent from the following Detailed Description and the figures.

DETAILED DESCRIPTION

Figure 1:
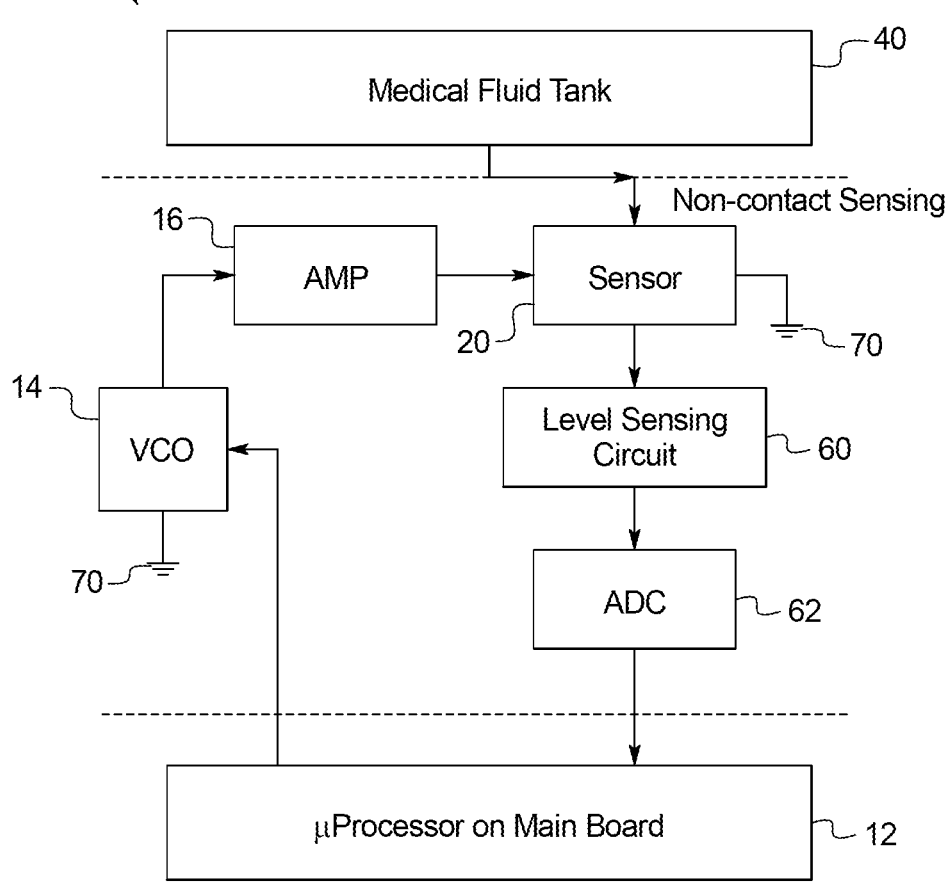
FIG. 1 is a schematic block diagram of one embodiment of the tank or container level or volume sensing system of the present disclosure.

Referring now to the drawings and in particular to FIG. 1, a system diagram for one embodiment of the container level or volume sensing system 10 is illustrated. System 10 includes a microprocessor and associated memory 12, which can be a delegate processor that communicates with a master or primary processor of a medical device into which system 10 is installed. Microprocessor and associated memory 12 can be located locally with the sensor of system 10. Alternatively, microprocessor and associated memory 12 are located remotely from the sensor of system 10, for example, in a safe place away from the fluid components of the medical fluid system. Microprocessor 12 can communicate with one or more memories to provide the functionality discussed herein.

In FIG. 1, microprocessor and associated memory 12 controls a voltage-controlled oscillator ("VCO") 14. VCO 14 in an embodiment is selected to produce an alternating signal, which can be in a radio frequency range, e.g., from about thirty kilohertz to about three-hundred gigahertz. VCO 14 can be an off-the-shelf component, which can produce the radio frequency as a sine wave or square wave. Oscillator 14 is powered via a voltage $V_{cc}$, which can for example be 5V. Voltage $V_{cc}$ can be obtained from a power source located on control board 100 or from a power source located elsewhere. Oscillator 14 is also connected to ground 70, which can be a system ground or earth ground. Power amplifier 16 is powered via a separate power supply the $V_{dd}$, which can for example be 5V. Power amplifier 16 is also taken to ground 70. The amplified RF signal from power amplifier 16 is sent via a coaxial wire to a connection point that is connected, for example via a wire-carrying ribbon or cable to a signal electrode of sensor 20, which operates as a transmission line as described below.

The RF signal from VCO 14 is amplified via a power amplifier ("AMP") 16. In one embodiment, the RF signal from VCO 14 is a very low power signal, e.g., in the range of about −20 to 5 dBm (the power ratio in decibels of the measured power referenced to one milliwatt). AMP 16 or an attenuator amplifies or attenuates the RF signal to about −10 dBm.

The amplified RF signal emanating from AMP 16 is then sent to sensor 20, which is discussed in detail herein. In general, however, sensor 20 is positioned operably adjacent to or onto a medical fluid tank 40, as shown in detail below. Sensor 20 in essence opens or allows the electric field associated with the RF signal to travel through the medical fluid tank 40. The ability of the electric field associated with the RF signal to travel through the medical fluid tank 40 is dependent upon how much fluid resides in tank 40. That is, the impedance to the RF signal transmission along transmission line sensor 20 is dependent upon how much liquid resides within the tank 40. Accordingly, a level sensing circuit 60 is provided to determine the overall impedance that sensor 20 sees. The level sensing circuit 60 may also determine the resistance or phase shift that sensor 20 sees.

By measuring the impedance seen by the electric field associated with the RF signal passing through container or tank 40, the sensing system 10 can determine the level of medical fluid within tank 40. By knowing the geometry of tank 40, the level sensing circuit therefore also enables a volume of liquid within tank 40 to be determined accurately and in real time. The impedance measured from sensor 20 is compared to a reference value, yielding a duty cycle that can be digitized by an analog-to-digital ("A/D") converter 62. The sampling rate can be varied from milliseconds to several seconds depending upon the need.

Delegate processor 12 reads digitized signal 62 and, for example in cooperation with one or more memories, converts the digitized signal into a value corresponding to tank or container fluid level or volume. It is contemplated that in a therapy or fluid to patient delivery situation, processor 12 queries a control board for system 10 for an impedance reading every so often, for example, every minute, to know and help maintain a desired fluid level in essentially real time. In a mixing situation, readings can be taken much more frequently, for example, on the order of milliseconds.

Figure 2:
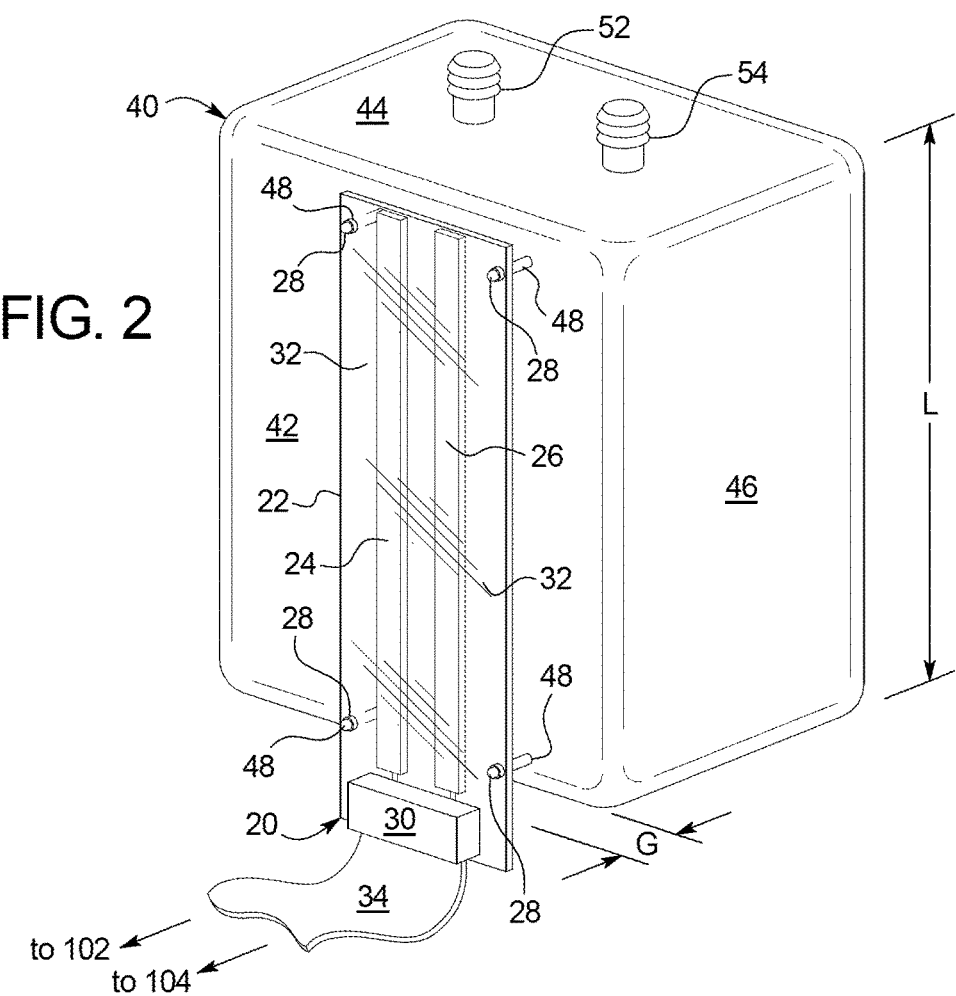
FIG. 2 is a front elevation view of one embodiment for the tank or container level or volume sensor of the present disclosure.

Referring now to FIG. 2, one embodiment for sensor 20 is illustrated. In the illustrated embodiment, sensor 20 is positioned directly adjacent to a fluid tank or container 40. Tank or container 40 is illustrated as being generally rectangular, having a front wall 42, top wall 44 and side wall 46. It should be appreciated however that container 40 can have other shapes as desired. In an embodiment, container 40 includes at least one relatively flat surface, such as front wall 42, adjacent to which sensor 20 is located. Otherwise, the other surfaces, such as top surface 44, side surface 46, and the back surface of container 40 can have projections, undulations, be rounded, curved or otherwise non-planer. In the illustrated embodiment, top wall 44 includes an inlet port or connector 52 for fluid-tightly receiving a fluid inlet tube for the medical device and a fluid outlet port or connector 54 for fluid-tightly receiving a fluid outlet tube of the medical device or system. In one embodiment, the RF wave propagates in a direction perpendicular to the top wall 44.

Sensor 20 includes a substrate 22, which can be made of any suitable non-conducting material, such as FR-4 material, ceramic, plastic, a polyimide, glass and any combination thereof. Substrate 22 includes a signal electrode 24 and a ground electrode 26. Electrodes 24 and 26 are made of a suitable conductive material, such as copper, nickel, gold, silver, lead, tin and alloys and combinations thereof. Electrodes 24 and 26 are electrochemically, photo-chemically, and/or mechanically plated, adhered, soldered, sputtered or sprayed onto substrate 22. For example, electrodes 24 and 26 can be copper electrodes formed on an FR-4 material via a known photo-etching process, which can provide a very detailed shape and geometry for electrodes 24 and 26.

In an embodiment, electrodes 24 and 26 have the same length or length that is very close to the length L corresponding to a full liquid level within container 40, which may or may not be the largest vertical dimension of the container. That is, substrate 22 is positioned relative to container 40, such that the bottom of electrodes 24 and 26 are aligned with the bottom of container 40, while the top of electrodes 24 and 26 are aligned with the top 44 of container 40. Alternatively, if a full level within container 40 is some level below top 44, then the top of electrodes 24 and 26 are instead lowered to this full level.

Electrodes 24 and 26 are shown facing outwardly from substrate 22 and container 40. Alternatively, electrodes 24 and 26 can be placed on the inside of substrate 22 so as to be located between substrate 22 and container 40. In either case, it is contemplated to space substrate 22 and electrodes 24 and 26 very close to surface 42, such as from about one-half millimeter (0.02 inch) to about five millimeters (0.197 inch). The widths of electrodes 24 and 26 can be varied as desired to provide a geometry that functions well with the RF signal generated from the VCO 14. One example width range is about a half centimeter (0.196 inch) to 1.5 cm (0.6 inch) for each of electrodes 24 and 26. The electrodes 24 and 26 can be spaced apart from each other by the approximate width of electrodes or some distance less than the electrode widths, such as being spaced apart one centimeter or less. The application thickness of electrodes 24 and 26 can be the standard application thickness for whatever process is used to form the electrodes. For example, an application thickness of about 20 to 100 micrometers is suitable in one embodiment.

As discussed below, sensor 20 is calibrated so as to yield a look-up table that processor 12 uses to correlate signal data to fluid level and/or fluid volume. When the geometry (e.g., size and/or spacing) of electrodes 24 and 26 is modified, the calibration needs to be performed again. It is contemplated to check the calibration for the particular geometry of electrodes 24 and 26 at the beginning of a pre-therapy (e.g., prime), therapy or post-therapy (e.g., rinseback or disinfection) procedure that uses system 10 and sensor 20. Here, a known quantity of the liquid is delivered to container 40. The reading taken by system 10 is compared to the known quantity or its associated fluid level. If the reading agrees with or is only slightly different than the known quantity, the calibration is maintained and used for the procedure. If disagreement between the reading and the known quantity is great, then liquid is either removed from or added to container 40 and the comparison procedure is repeated. If after a number of calibration checks it is found that the reading is off by a consistent delta, each value of the calibration look-up table is modified by the consistent delta and a modified calibration is used for the procedure. If after a number of calibration checks it is found that the reading is off by a non-consistent delta, processor 12 can take an average of the deltas and modify each of the values of the calibration look-up table by the average delta to form a modified calibration that is used for the procedure. If the reading is found to vary an unacceptable amount from the known quantity, then processor 12 causes the medical device to post an alarm.

In the illustrated embodiment, substrate 22 is mounted to studs 48 extending from surface 42 of container 40, so as to be set precisely at gap distance G. In an alternative embodiment, substrate 22 is mounted to a fixed portion of the medical machine independent of container 40 or the fixture for container 40. In the illustrated embodiment, substrate 22 can be provided with apertures 28 that snap fit into grooves positioned precisely along studs 48 of container 40, so as to set a gap distance G that does not vary even if container 40 is vibrated or moved slightly during the functioning of the medical device.

Electrodes 24 and 26 in the illustrated embodiment terminate at a terminal block 30 located, for example, below the bottom of container 40. Terminal block 30 connects to a protective ribbon or cable 34, which can for example be flexible and insulating, and which in turn leads to coaxial line 102 and ground line 104 of control board 100 shown in FIG. 4.

A protective coating, such as a conformal or epoxy coating 32 is sprayed or laminated over electrodes 24 and 26 and elsewhere along substrate 22 and terminal block 30 as needed to ensure that the wetness, humidity and heat potentially generated within the medical device does not harm or degrade the components and/or performance of sensor 20 and system 10. Substrate 22 in an alternative embodiment is made part of or placed within a protective housing (not illustrated), such as a protective plastic housing.

Figure 3:
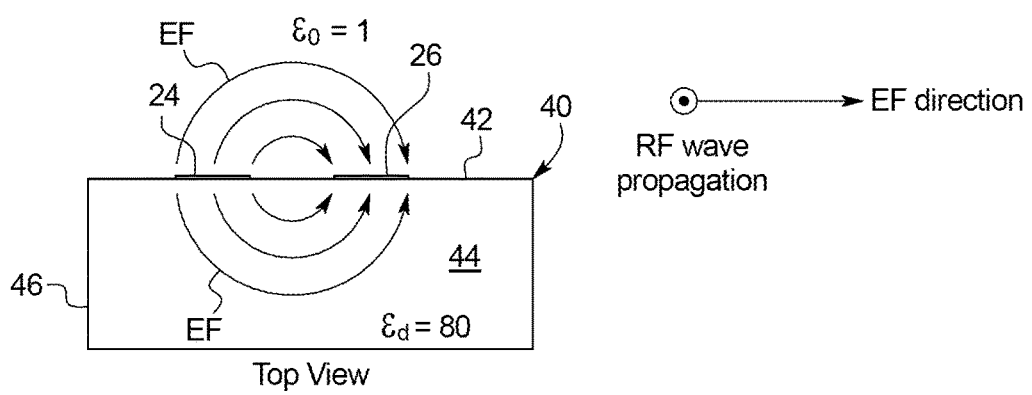
FIG. 3 is a schematic view showing the electric field generated from the signal electrode of the sensor to the receiving electrode of the sensor.

Referring now to FIG. 3, the operation of electrodes 24 and 26 of the sensors of FIG. 2 is illustrated. FIG. 3 is a top view of a container 40. Here again, electrodes 24 and 26 are placed adjacent to or on front surface 42 of container 40. When the energy source is activated, an electric field is created between signal electrode 24 and ground electrode 26, in which the electric field lines travel from the positive emitter 24 to the negative receiver 26. The direction of the electric field is parallel to the top surface of a fluid in one embodiment. In other words, the direction of the electric field is parallel to a plane defining the level of the fluid in the tank. The electric field carries an RF signal, in which the propagation of the RF wave is perpendicular to the direction of the electric field lines. Thus the electrical field is generated from positive electrode 24 to negative electrode 26, and the RF wave propagates along the electrodes.

The electric field carrying the RF signal travels from signal electrode 24 to ground electrode 26 in two directions as shown in FIG. 3, namely, through a first path along the outside of container 40 and through a second path along the inside of container 40. Thus, a portion of the electric field travels through a fluid and the remainder of the electric field travels through free space. As the fluid level inside the tank is lowered, more and more of the electric field travels through free space. In one embodiment, as less of the electric field is covered by the fluid, the effective load of the modeled transmission line changes.

The path along the outside of container 40 is modeled in the illustrated example as being solely through air, which has a dielectric constant of free space, $\in_0$ equal to one. Assuming for sake of example that container 40 is completely full of liquid water, the path for the RF signal on the inside of container 40 is solely through a medium having a dielectric constant of water, $\in_d$ equal to approximately 80. It is assumed that any fluid that will reside within container 40 is either water or a substantially water-based medical fluid, such as dialysate for hemodialysis and peritoneal dialysis, replacement fluid for hemofiltration and hemodiafiltration, and any operating room drug or liquid, such as saline.

There is then an equivalent dielectric, ∈, which is equal to $\in_0$ plus $\in_d$ divided by two. Thus if tank 40 is completely empty, a dielectric environment $\in_0$ for air will exist on the outside and the inside of the tank, resulting in an equivalent dielectric being one plus one divided by two, which equals one, the dielectric constant of free space. As water or medical fluid fills container 40, the dielectric constant of air is continuously replaced by more and more media having the dielectric constant of water, until container 40 is completely full, at which point the equivalent dielectrics is equal to approximately (1+80)/2 or 40.5. In this manner, the characteristic resistance of the tank imparted to the RF sensor varies as a result of the effective equivalent dielectric varying anywhere from 1 to 40.5.

As the water or medical fluid level changes, the overall dielectric constant also changes. Specifically, as the fluid level inside of the tank decreases, the overall dielectric constant, which can be approximated as averaging the dielectric constant inside the tank plus the dielectric constant outside the tank divided by two, also decreases. When the overall dielectric constant decreases, the impedance measured by the circuitry attached to the sensor also decreases.

The characteristic impedance $Z_0$ varies according to the formula $$Z_0 = \sqrt{\frac{\mu o}{\varepsilon}} F(g),$$

where $\mu_0$ is the permeability of free space, which is a constant, and F(g) is a function of the geometry of the RF transmission line, including electrodes 24 and 26. The electrodes are accordingly sized and shaped to be optimized via their geometry to provide a changing output having a desirable accuracy, linearity, repeatability and robustness for a particular geometry of tank 40.

The system is calibrated so that it is known how much fluid corresponds to an impedance. Once the transmission line has been established and calibrated, the electronic circuitry attached to the sensor can monitor various parameters to determine the level of the tank. As described above, the two electrodes can be used to model a transmission line. The RF wave sent into the transmission line, i.e., the incident wave, propagates along the transmission line and is then affected by the load or impedance of the tank. The wave reflects back, creating the reflected wave, and the difference in characteristics between the incident wave and the reflected wave can be used to determine the water level of the tank. The difference in characteristics between the two waves depends on the equivalent dielectric constant at that water level. In other words, a change in water level leads to a change in the equivalent dielectric constant, which leads to a change in the measured values of the incident and reflected waves.

In one embodiment, the electrodes can model a slot line transmission line. Construction of a slot line transmission line is well known in the art. See, for example, Holzman, Essentials of RF and Microwave Grounding, p. 60 (2006); Gupta, Microstrip Lines and Slotlines, 2nd Edition, Artech House Microwave Library, pp. 269 to 340 (1996); S. B. Cohn, Slot-line—An Alternative Transmission Medium for Integrated Circuits, IEEE G-MTT International Microwave Symposium Digest, pp. 104 to 109 (1968), which are incorporated herein by reference.

Parameters that affect whether the electrodes operate as a reliable slot line transmission line include, for example, the frequency of the system, the distance of the electrodes from the tank, the width and thickness of the electrodes, and the distance between the electrodes.

Figure 4:
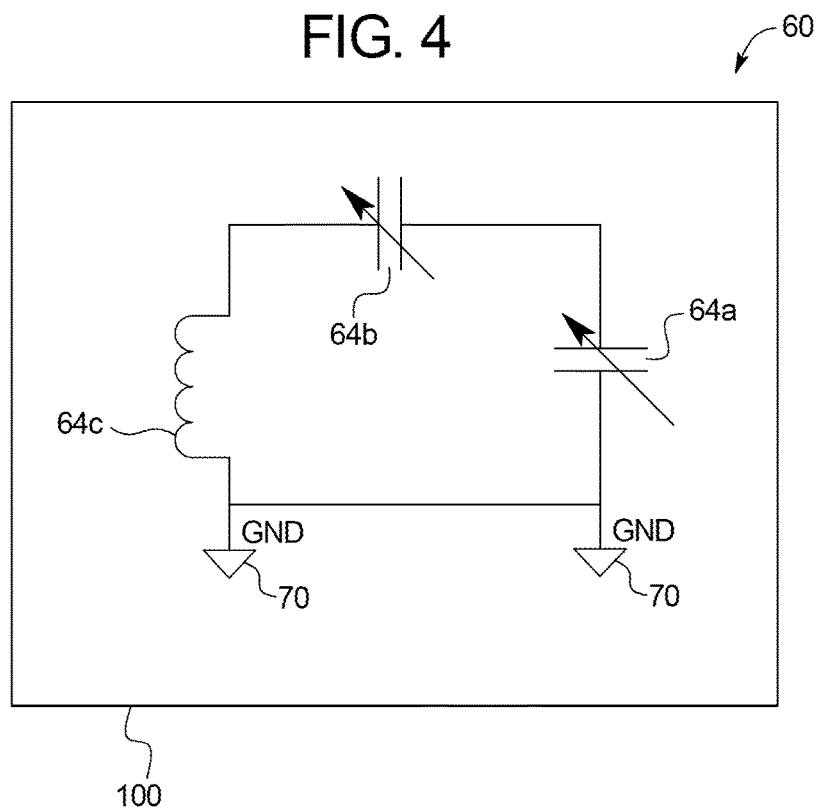
FIG. 4 is an electrical schematic of one embodiment of the tank or container level or volume sensing system of the present disclosure.

Referring now to FIG. 4, a control board 100 provides an example embodiment of level sensing circuit 60 that can be used in system 10 that correlates the resistive component of impedance to a water fluid level. Control board 100 includes components 12, 14, 16 and 62 (not shown) and connects to sensor 20 (not shown). In particular, control board 100 includes oscillator or VCO 14, which is connected via a computer link to processor 12 as show in FIG. 1. Although not illustrated in FIG. 4, system 10 in one embodiment provides a filter, such as a low pass filter, that removes the DC component from the amplified signal. Control board 100 also includes a return or ground connection point connected to sensor 20 via the cable or ribbon. The return or ground connection point runs via a return line 104 to ground 70. The filter is also taken to system or earth ground 70.

Figure 6:
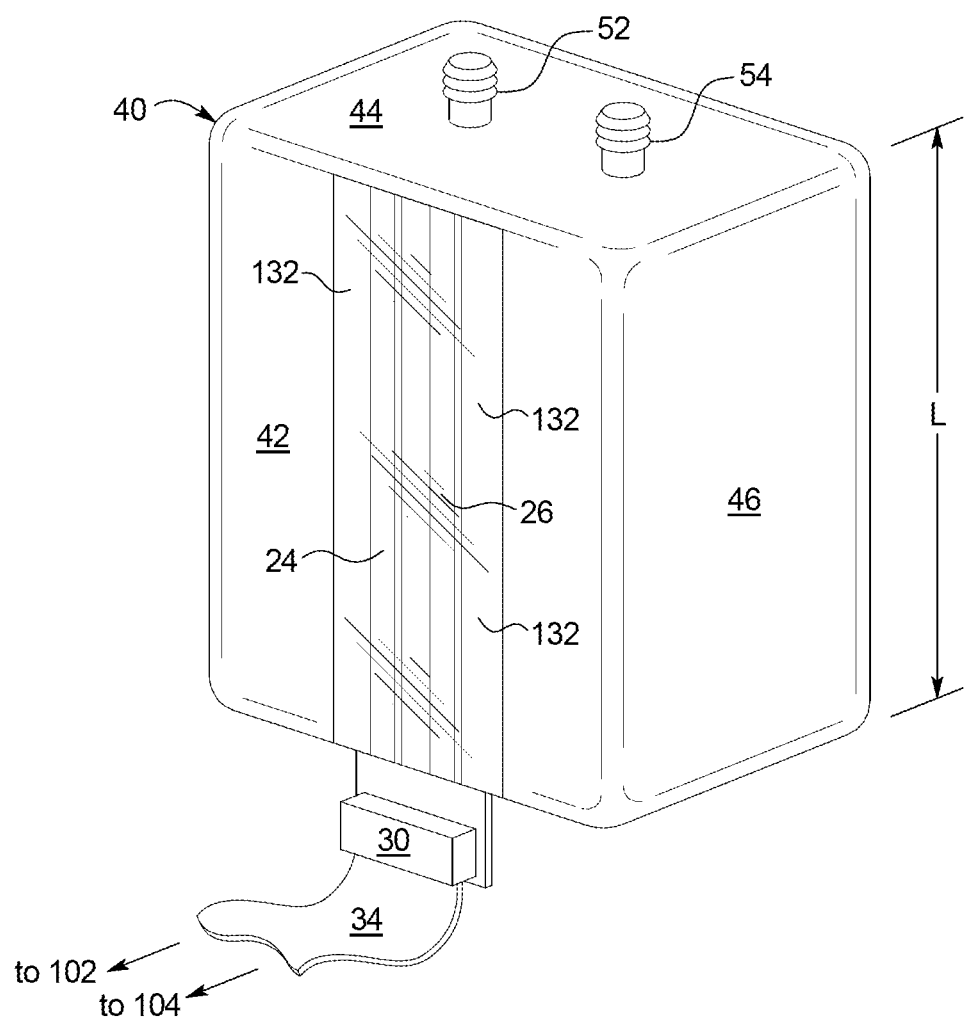
FIG. 6 is a front elevation view of another embodiment for the tank or container level or volume sensor of the present disclosure.

It is contemplated to locate control board 100 in a safe electronics area of the medical fluid device, for example, away from potential splashing and heat generated within the medical fluid machine. It is further contemplated to locate microprocessor and associated memory 12 of system 10 on a board that is separate from control board 100. That is, processor 12 could be a remote microprocessor that controls other functions of the medical device, for example, other functions related to the pumping of medical fluid to and from the medical fluid tank 40 (FIGS. 2 and 6).

Control board 100 of FIG. 4, which is one embodiment of the level sensing circuit 60 of FIG. 1, is tapped off of coaxial wire 102 of FIG. 2 (not shown). Control board 100 analyzes the resistance along coaxial wire 102 via components 64a, 64b and 64c. Components 64a, 64b and 64c are capacitors and inductors that can be tuned during calibration to minimize the impact from the imaginary part, or reactance, of the impedance. In an experiment for sensor 20, the results of which are discussed below with FIGS. 8 to 10, level sensing circuit 60 of control board 100 was structured such that capacitor 64a had a value of 2.7 pF, capacitor 64b had a value of 5.6 pF and inductor 64c had a value of 1.8 nH. Using these values for the capacitors and inductors, a tuning circuit operating at 1.4 GHz drove the reactive part of the impedance to zero effectively. These values are merely examples of suitable values and are non-limiting. That is, other values, and perhaps other types of tuning circuits may be used for the same or different frequency.

A comparator (not shown) is provided which compares the output of level sensing circuit 60 to a reference signal. The comparator is powered via the same voltage $V_{dd}$ that powers power amplifier 16. Voltage $V_{dd}$, like voltage $V_{cc}$, can be obtained from a source located on control board 100 or from a source located elsewhere within the medical device. The signal from the comparator is digitized via analog-to-digital digital converter 62, shown above in FIG. 1. The digitized signal is sent to processor 12, as has been discussed herein. Processor 12 operates with one or more memories that in one embodiment store a pre-loaded or pre-stored look-up table that has been created from a prior calibration of sensor 20. Processor 12 uses the look-up table to match the digitized instantaneous or real-time signal to a corresponding tank fluid level. Since the geometry of the tank is known, any tank fluid level can be correlated to a tank fluid volume. In this manner, processor 12 can alternatively or additionally match the instantaneous or real-time signal to a tank fluid volume.

Figure 5:
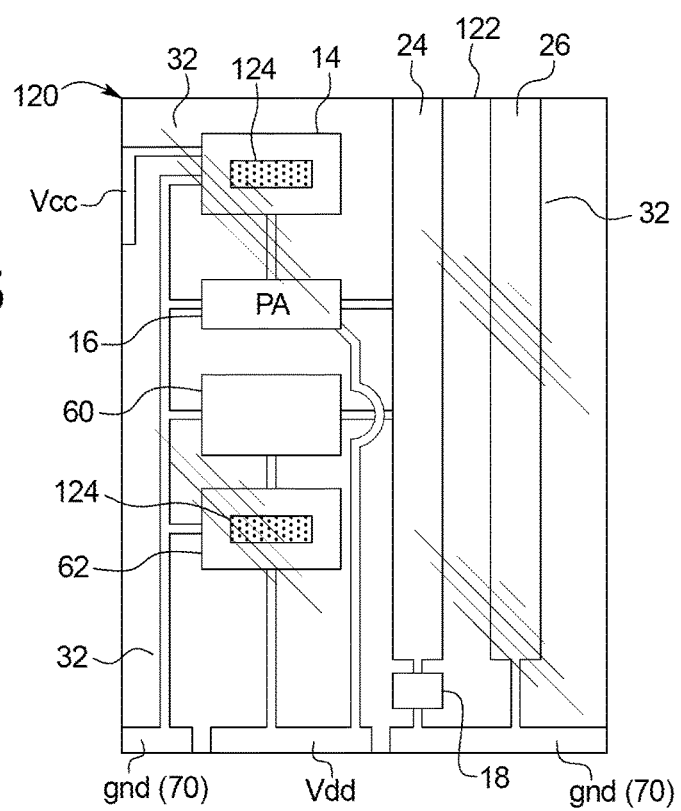
FIG. 5 is a front view of one alternative embodiment for a control board of the sensor of the present system and method.

Referring now to FIG. 5, an alternative control board 120 is illustrated. Here, the electronics associated with control board 100 (FIG. 4) are located on the same insulative substrate 122 along with signal electrode 24 and ground electrode 26 of FIG. 2. Substrate 122 can be formed of any of the materials discussed above for substrate 22. Electrodes 24 and 26 can be of any of the materials, have any of the geometries and be applied in any of the manners discussed above for electrodes 24 and 26 of FIG. 2. In control board 120, components such as VCO 14, power amplifier 16, filter, level sensing circuit 60, A/D converter 62 and comparator described above are also located on the same board as sensing elements 24 and 26. In an embodiment, the components communicate electrically via traces photo-etched onto substrate 122.

The respective components shown in FIG. 4 running to ground 70 are also shown in FIG. 5 running to ground terminals 70, which are then connected to system or earth ground when control board 120 is plugged into place. Likewise, a voltage terminal $V_{dd}$ is plugged into a voltage line that powers the comparator and power amplifier 16. Still further, a voltage terminal $V_{cc}$ is connected to a voltage source powering VCO 14. A conformal, epoxy or other suitable protective coating 32 is applied over the electrodes and electrical components of control board 120 as needed to protect such components from the operating conditions residing within the medical device. Besides the ground and voltage connection, VCO 14 and A/D converter 62 are configured to communicate with processor 12 (located for example on a remote processing board) via data signal connectors 124, such as universal serial bus ("USB") connectors.

Referring now to FIG. 6, a further alternative configuration for the sensor 20 of system 10 is illustrated. In the illustrated embodiment, electrodes 24 and 26 are applied directly to surface 42 of container 40 via an adhesively coated protective film 132, so as to eliminate the separate substrate 122. Adhesive film 132 can be any suitable non-conducting and water impermeable film, such as a plastic or polymer film. Signal electrode 24 and ground electrode 26 are applied first to the sticky or adhesive side of film 132. Film 132 is then taped to surface 42 of container 40. Alternatively, electrodes 24 and 26 are applied first to surface 42, followed by protective film 132.

Film 132 extends with electrodes 24 and 26 so that the electrodes connect electrically to a terminal connector 30, which in turn connects further to cable or ribbon 32 that extends leads to coaxial line 102 and ground line 104 located safely within the medical device machine at control board 100. In an embodiment, the wall thickness of surface 42 is sized to ensure that electrodes 24 and 26 are spaced an adequate distance away from the interior of container 40. Alternatively, if needed, spacers, such as non-conductive spacers, can be used to set electrodes 24 and 26 away from the interior of container 40.

It is contemplated in any of the sensor configurations discussed herein to locate electrodes 24 and 26 away from other conductive materials within the medical device a certain distance, such as about one centimeter (0.394 inch) or more. The spacing helps the operation of the sensor, discussed above.

Figure 7:
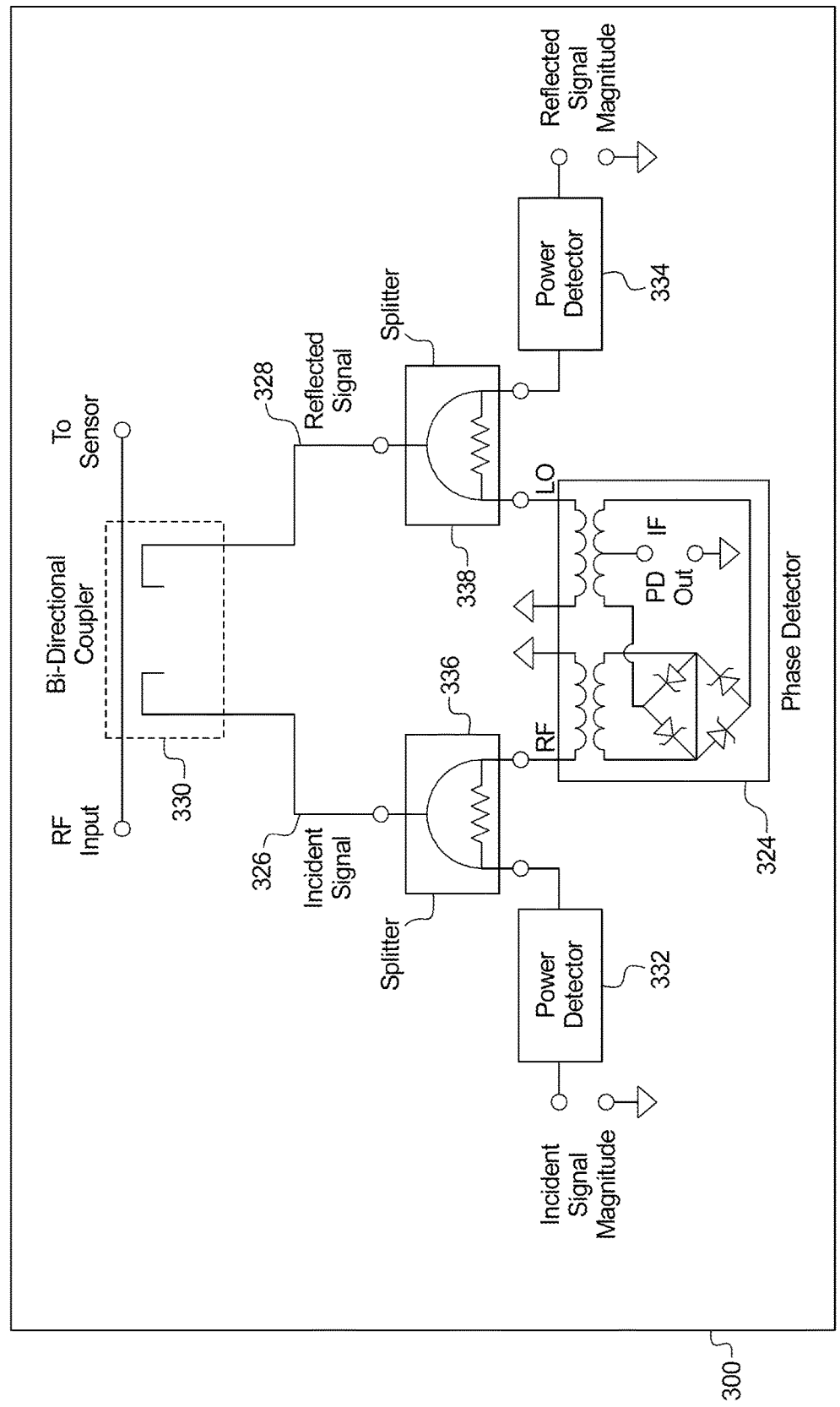
FIG. 7 is an electrical schematic of another embodiment of the tank or container level or volume sensing system of the present disclosure.

FIG. 7 is a circuit diagram of an example control board 300 used with the sensor 20 of system 10 for determining a fluid level using the impedance seen by an RF wave. Control board 300 includes components 12, 14, 16 and 62 (not shown) and connects to sensor 20 (not shown). In particular, control board 300 includes a microprocessor (FIG. 1) and associated memory 12, which control a voltage-controlled oscillator ("VCO") 14. Control board 300 operates with sensor 20, which can be implemented in any of the configurations discussed above, e.g., with FIG. 2, 5 or 6. Electrodes 24 and 26 (not shown) are connected electrically to the circuitry of control board 300. The electrical connection of electrodes 24 and 26 from sensor 20 to control board 300 can be by flexible cable, insulated wire, or via any of the ways discussed herein for system 10.

It is contemplated (as with control board 100) to locate control board 300 in a safe electronics area of the medical fluid device, for example, away from potential splashing and heat generated within the medical fluid machine. It is further contemplated to locate microprocessor and associated memory 12 of system 10 on a board that is separate from control board 300. That is, processor 12 could be a remote microprocessor that controls other functions of the medical device, for example, other functions related to the pumping of medical fluid to and from the medical fluid tank 40 (FIGS. 2 and 6). In an embodiment, control board 300 can be implemented on a printed circuit board ("PCB", e.g., FR-4 or other type listed above), which can be about two inches by two inches (e.g., about five cm by five cm).

Control board 300 includes frequency mixing circuitry 324, which generates an electrical, e.g., millivolt ("mV") output, which is particular for a certain electrical length or level. In one implementation, RF and LO ports on mixing circuitry 324 are used for the forward, or incident, signal 326 and the reflected signal 328, respectively, from bi-directional coupler 330, and an IF port on the mixing circuitry 324 is used as the sensed output. Because the frequencies of the forward signal 326 and reflected signal 328 are the same, and the forward phase is constant, the output from the IF port results in phase information of the reflected signal, which can be used to determine the liquid level within tank 40.

Oscillator 14 generates a sinusoidal signal at a desired and selected frequency as the RF input on control board 300. The signal is transmitted through bi-directional coupler 330 to the transmission line (not shown). The bi-directional also outputs an incident signal as well as a reflected signal. The incident signal includes a magnitude and a phase for the signal going from the VCO 14 to the probes 24 and 26.

The signal transmitted to the transmission line will be reflected in part due to the impedance of the tank 40 as well as any mismatch of the transmission line. As is known in the art, impedance matching circuitry can be used to reduce impedance mismatching, such as, for example, by shifting impedances to the real axis of a Smith chart as much as possible. In one embodiment, any reflection due to a mismatch is ignored or eliminated, leaving only the reflection due to the impedance of tank 40. The reflected signal 328 can be measured at the reflected signal output of bi-directional coupler 330. The reflected signal includes a magnitude and a phase for the signal reflected from the probes 24 and 26. In the illustrated embodiment, the incident signal 326 is then split into magnitude and phase results by splitter 336, and reflected signal 328 is split into magnitude and phase results by splitter 338. Power detectors 332 and 334 are used to measure the magnitudes of the incident signal 326 and reflected signal 328, respectively. Phase detector circuit 324 (frequency mixer) can measure the phase difference between the incident and reflected signals.

A network analyzer, such as for example, ENA Series Network Analyzer (E5071C), can be used to analyze S-parameters that provide information about the incident signal, reflected signal, and phase shift. The S-parameters are expressed in terms of magnitude and the phase, where the splitters separate the magnitude and phase results, providing magnitude results to the power detectors and providing phase results to the phase detector. The power detectors 332 and 334 convert magnitude results into voltages representing the magnitudes of the incident and reflected signals, respectively. The ratio of the magnitudes of the incident signal to reflected signal can be used to determine a reflection coefficient. Phase detector circuit 324 converts phase results into a voltage representing the difference in phase between the incident signal and the reflected signal.

With measurements of the reflection coefficient and the phase shift, the impedance seen by the transmission line can be determined. The impedance corresponds to a level of medical fluid in the tank, and thus medical fluid level can be determined. This operation can be confirmed with a Smith chart, where a reading of the reflection coefficient and phase angle can be correlated to an overall impedance.

The components used during experimentation are readily available and can be implemented as described herein by those skilled in the art. For example, component-provider Minicircuits manufactures bi-directional couplers (e.g., model number ZX30-20-20BD+), power detectors (e.g., model number ZX47-50LN+), VCO (e.g., model number ZX95-1600W+), phase detectors (e.g., model number ZFM-5X+), and power splitters (e.g., model number ZX10R-14+) that may be used in control board 300 of FIG. 7.

Figure 8:
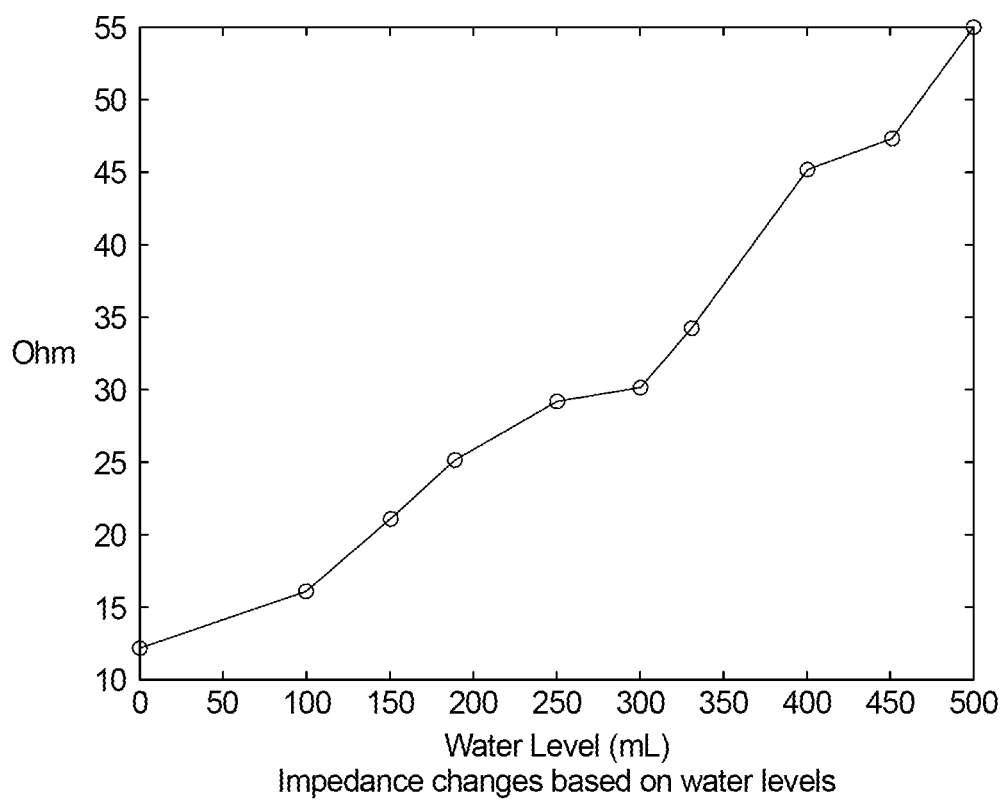
FIG. 8 is a graph illustrating results from testing of the RF transmission level or volume sensing system of the present disclosure.

FIG. 8 illustrates results from preliminary testing of system 10. FIG. 8 shows a roughly linear change in impedance over a liquid level change of five-hundred millimeters. It is believed that the results can be made even more linear and repeatable by experimenting with different geometries and materials for electrodes 24 and 26. Further, a constant cross-sectional tank will likely yield more linear results. It should also be appreciated that the impedance change in FIG. 8 is the steepest, and thus the most sensitive, in the middle of the curve, flattening out at the beginning and end of the curve. It is contemplated then to match the expected high and low levels of the fluid within tank 40 with the middle or steep range of the sensor output curve shown in FIG. 8. In this manner, the liquid level is likely to vary within the most sensitive range of sensor 20.

It is accordingly contemplated to store in processor 12 and its associated memory a database correlating a particular impedance, resistance or reactance to a particular liquid level within a water or medical fluid holding tank, such as tank 40. The correlation table is determined for the tank and sensor electrode geometries. It should be appreciated that, assuming the correlation table takes into account the full range from completely empty to completely full, a medical device can look at the tank level at any desired time and receive an up-to-date, real-time indication of liquid level. And as has been described herein, especially in certain medical applications, it is advantageous that the system 10 level sensing is not dependent on liquid conductivity.

Test data can be used to confirm that the impedance output of the sensor is relatively insensitive to conductivity. A propagation constant for the RF signal of sensor 20 is a measure of a change undergone by the amplitude of the RF wave as it propagates through the changing tank fluid level. The propagation constant measures change per unit length but is otherwise dimensionless. The propagation constant can be expressed as follows:

$$\text{Propagation constant: } \gamma = \sqrt{(R_{conductor} + j\omega L)(G + j\omega C)}$$

$$= \sqrt{\left(\frac{R_{conductors}}{F(g)} + j\omega\mu_0\right)(\sigma_d + j\omega\varepsilon)}$$

Such that: $L = \mu_0 F(g) \ \ C = \varepsilon/F(g) \ \ G = \sigma_d/F(g)$

The transmission line impedance for sensor 20 can be derived from the above propagation constant equations as follows:

$$Z = \sqrt{\frac{R_{conductors} + j\omega L}{\gamma}}$$

$$= \sqrt{\frac{R_{conductors} + j\omega L}{G + j\omega C}}$$

$$= \sqrt{\frac{\frac{R_{conductors}}{F(g)} + j\omega\mu_0}{\sigma_d + j\omega\varepsilon}} \cdot F(g)$$

For the above equation for impedance Z, $R_{conductors}$ can be considered to be zero (because transmission line electrodes 24 and 26 are good conductors) and F(g) can be considered to be equal to one for a slot line break between electrodes 24 and 26. The transmission line impedance Z can then be simplified to:

$$Z = \sqrt{\frac{j\omega\mu_0}{\sigma_d + j\omega\varepsilon}}$$

$$= \sqrt{\frac{j\sigma_d\omega\mu_0 + \omega^2\mu_0\varepsilon}{\sigma_d^2 + \omega^2 + \varepsilon^2}}$$

$$= \sqrt{\frac{\mu_0}{\varepsilon}} \cdot \sqrt{\frac{j\tan\delta + 1}{\tan^2\delta + 1}},$$

where $\tan \delta = \frac{\sigma_d}{\omega\varepsilon}$ is the loss tangent.

In one example calculation, frequency (f) for RF is taken to be 1.4 GHz. $\sigma_d$ is used for different conductivity settings ranging as follows: (i) 15 mS/cm, (ii) 10 mS/cm, (iii) 5 mS/cm, and (iv) 0 mS/cm. The dielectric constant $\in = \in_r$ to $\in_0$; where $\in_r$=80 and $\in_0$=1, resulting in:

TABLE 1

| |
|---|
| for $\sigma_d$ = 15 mS/cm → Z = 41.1411 + 4.8846i |
| for $\sigma_d$ = 10 mS/cm → Z = 41.6195 + 3.3201i |
| for $\sigma_d$ = 5 mS/cm → Z = 41.9172 + 1.6799i |
| for $\sigma_d$ = 0 mS/cm → Z = 42.0183 |

As illustrated in Table 1 above, which was obtained according to the above equations using MATLAB® software, no significant change occurs in the first number (41.1411, 41.6195, 41.9172 and 42.0183), which corresponds to the real part of the impedance, or resistance, when the dielectric's conductivity changes from zero to fifteen mS/cm. Per the derived formulas, high frequencies minimize the change in overall impedance, explaining these results. The second number (4.8846i, 3.3201i, 1.6799i and 0i) corresponding to the imaginary part of the overall impedance, or reactance, may be tuned out of the results as shown via the electronics described above. The resulting transmission line sensor 20 is accordingly not sensitive to the liquid conductivity change at least in the range of zero to fifteen mS/cm.

Figure 9:
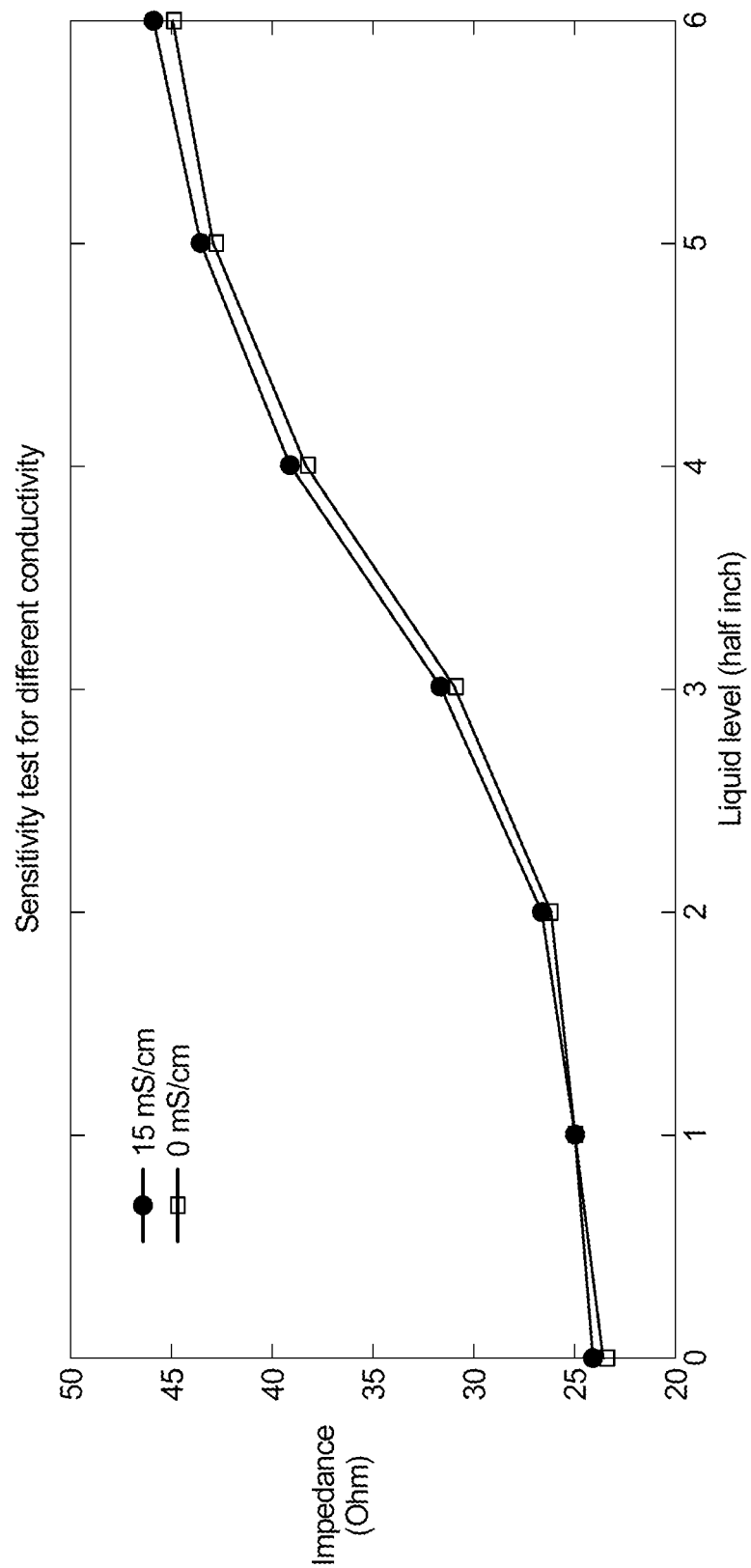
FIG. 9 is a plot of impedance versus tank liquid level for two liquids at two different conductivities showing that the impedance output of the sensor of the present disclosure is relatively insensitive to conductivity.

Referring to FIG. 9, an experimental plot for sensor 20 shows that there is very little difference in the output of the sensor when the conductivity changes from zero to fifteen mS/cm, which is a range that should encompass most of the medical fluids discussed herein. It is expected too that the conductivity could be increased past fifteen mS/cm without significantly affecting sensor output. The reason is due to the loss tangent (equation shown above) being small because a high, e.g., RF, frequency is used. Suitable frequencies for sensor 20 can be between one and two GHz.

Figure 10:
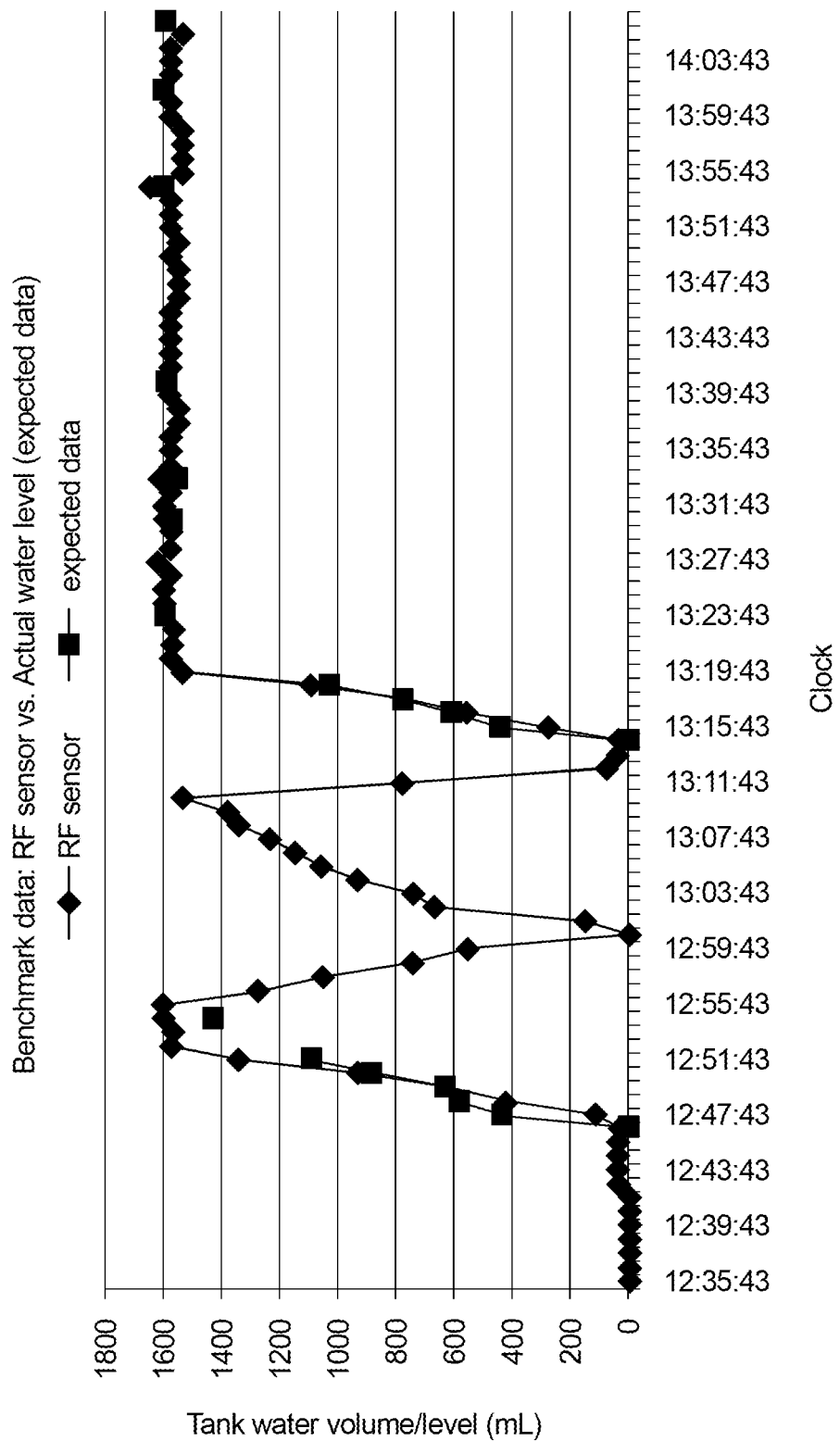
FIG. 10 is a plot of tank level/volume over time showing the accuracy of the output of the system and sensor of the present disclosure compared with expected tank level/volume data.

Referring now to FIG. 10, accuracy results using system 10 and sensor 20 are illustrated. The squares represent known or expected tank level or volume data. The diamonds represent tank level or volume using data from system 10 and sensor 20. As illustrated, the sensor output matches the expected output very well all the way through the tank volume range of zero to 1600 milliliters. As should be appreciated viewing the x-axis of the plot of FIG. 10, time increments between readings can be selected as desired to be on the order of minutes, seconds, or even fractions of seconds.

Figure 11:
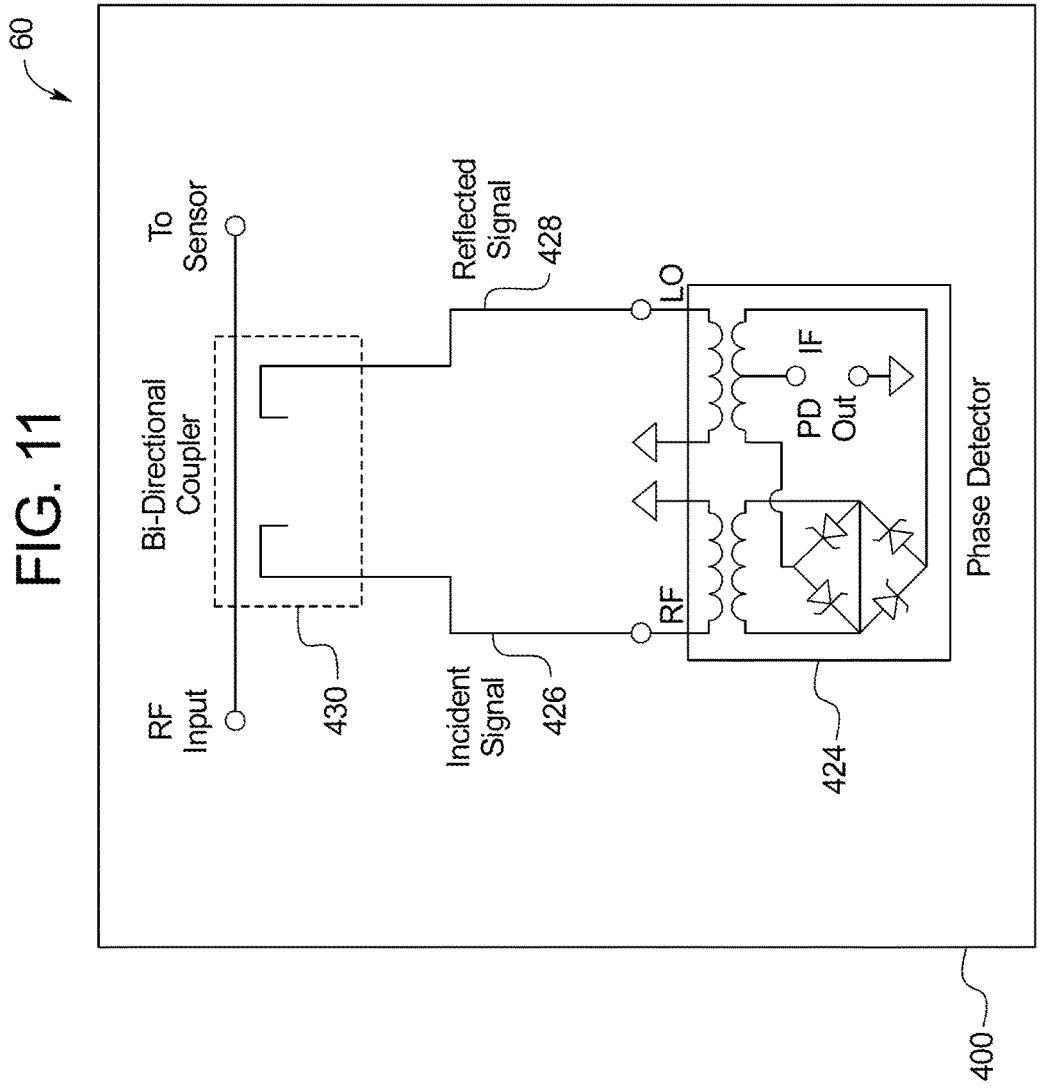
FIG. 11 is an electrical schematic of yet another embodiment of the tank or container level or volume sensing system of the present disclosure.

Referring now to FIG. 11, another embodiment for detecting tank level or volume non-invasively for a radio frequency or other high frequency system is illustrated in control board 400 for system 10. Control board 400 determines medical fluid level based on the phase component of the impedance or change in electrical length. In general, electrical length can be thought of as the length of a transmission line expressed as the number of wavelengths of a signal propagating in a medium. The high frequency or RF waves propagate more slowly in a medium, such as dialysis fluid, blood, dialysate, or a liquid drug, than in free space.

Sensor 20 and medical fluid tank 40 in FIGS. 2, 5 and 6, including all alternative embodiments discussed for sensor 20 (including all physical, structural and implementation alternatives for electrodes 24 and 26) and tank 40 can be used again in phase shift system implemented using control board 400. The radio frequency transmission model shown above in FIG. 3, which illustrates $\in_0$, the dielectric constant of free space, and $\in_d$, the dielectric constant of water, is likewise applicable to control board 400.

FIGS. 2 and 6 show that in one embodiment, electrodes 24 and 26 have the same length L as the height of tank 40, so that any liquid level within tank 40 can be detected. The physical length L of the transmission lines or electrodes 24 and 26 is a component of the electrical length. In particular, the electrical length, $\phi$, can be expressed as a function of the physical length of the transmission line L, and the dielectric of the medium through which it travels as follows:

electrical length, $\phi = \in * \beta_0 * L$, where $\in$ is the overall dielectric constant, $\beta_0$ is the number of waves for a given wavelength or frequency propagation that occurs in free space over a known distance, such as one meter, and is a constant stored in memory, and L is again the physical length of the transmission line or sensor, and is a constant stored in memory.

The overall dielectric constant $\in$ as shown in the equation above is a function of $\in_o$, the dielectric constant of free space, and $\in_d$, the dielectric constant of water, dialysate, drug, medicament or other water-based medical fluid. When the liquid level in tank or container 40 changes, the electrical length $\phi$ also changes according to the equation:

change in electrical length $\Delta\phi = 2\in_1\beta_0 L - 2\in_2\beta_0 L$, where $\in_1$ is the equivalent overall dielectric constant at liquid level 1, and $\in_2$ is the equivalent overall dielectric constant at liquid level 2.

The electrical length $\phi$ of free space can be calibrated for a particular configuration of tank 40 and electrodes 24 and 26, including the spatial relationship between tank 40 and electrodes 24 and 26 (as illustrated by different electrode mounting techniques shown in FIGS. 2 and 6).

The free space electrical length is stored in the memory of control board 400, which can be located in any of the configurations discussed above for system 10. When the level of liquid changes within tank 40, the overall dielectric changes, causing the electrical length of the signal propagated from electrode 24 to change. The circuitry above provides an output that is indicative of the new electrical length. The free space electrical length is subtracted from the newly sensed electrical length forming a $\Delta\phi$. A lookup table is stored in memory that correlates a particular $\Delta\phi$ with a particular tank level or volume. Thus, the tank level or volume can be known at any time and at any level within the tank.

Like control board 300 from FIG. 7, control board 400 in FIG. 11 measures the phase angle of the RF wave. Control board 400 includes frequency mixing circuitry 424, which generates an electrical, e.g., millivolt ("mV") output, which is particular for a certain electrical length or level. In one implementation, RF and LO ports on mixing circuitry 424 are used for the forward, or incident, signal 426 and the reflected signal 428, respectively, from bi-directional coupler 430, and an IF port on the mixing circuitry 424 is used as the sensed output. Because the frequencies of the forward signal 426 and reflected signal 428 are the same, and the forward phase is constant, the output from the IF port results in phase information of the reflected signal, which can be used to determine the liquid level within tank 40.

Oscillator 14 generates a sinusoidal signal at a desired and selected frequency as the RF input on control board 400. The signal is transmitted through bi-directional coupler 430 to the transmission line (not shown). The bi-directional also outputs an incident signal as well as a reflected signal. The incident signal includes a phase for the signal going from the VCO 14 to the probes 24 and 26.

As described above with respect to control board 300, the signal transmitted to the transmission line will be reflected in part due to the impedance of the tank 40 as well as any mismatch of the transmission line. As is known in the art, impedance matching circuitry can be used to reduce impedance mismatching, such as, for example, by shifting impedances to the real axis of a Smith chart as much as possible. In one embodiment, any reflection due to a mismatch is ignored or eliminated, leaving only the reflection due to the impedance of tank 40. The reflected signal 428 can be measured at the reflected signal output of bi-directional coupler 430. The reflected signal includes a phase for the signal reflected from the probes 24 and 26. Phase detector circuit 424 (frequency mixer) can measure the phase difference between the incident and reflected signals. As described above, phase detector circuit 424 converts phase results into a voltage representing the difference in phase between the incident signal and the reflected signal. Control board 400 in FIG. 11 does not however need to measure the magnitude of the incident and reflected waves, and instead relies on the reading of the phase to determine the tank level. The reading of the phase depends on the electrical length of the system.

Compared to control board 300 of FIG. 7, control board 400 of FIG. 11 thus contains less circuitry because control board 400 uses fewer voltages and readings than control board 300. For example, FIG. 7 requires power detectors that measure magnitudes of incident and reflected waves that FIG. 11 does not require. Because control board 300 of FIG. 7 uses additional voltages and readings, control board 300 may be used to provide a higher resolution sensor in certain embodiments.

Figure 12:
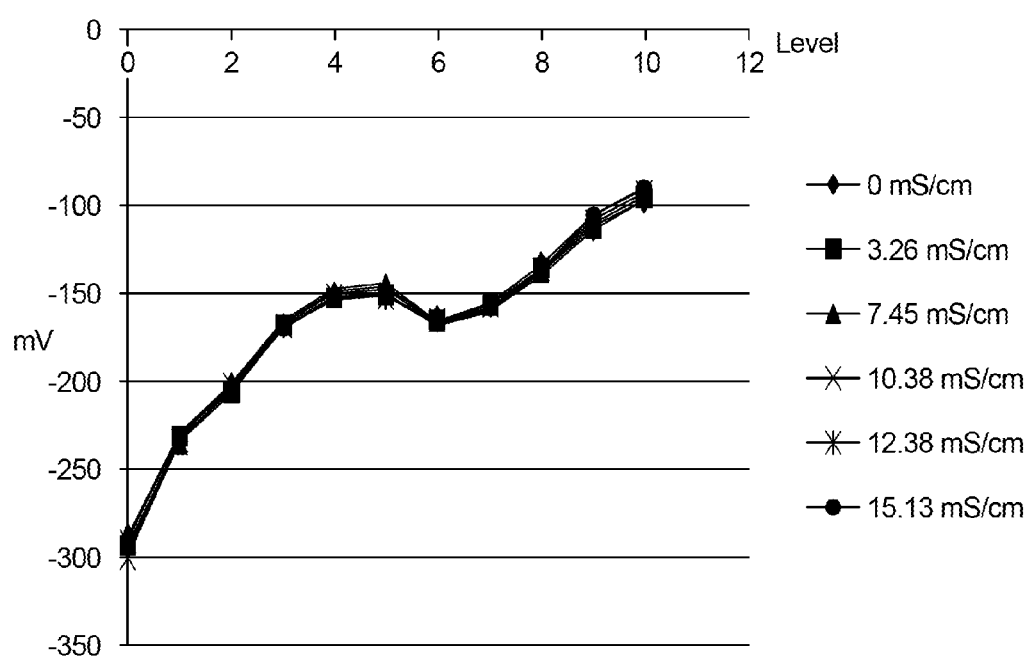
FIG. 12 is a plot of phase shift output versus tank liquid level for liquids at multiple different conductivities showing that the phase shift output of the sensor of the present disclosure is unaffected by conductivity.

Referring now to FIG. 12, an experimental plot for sensor 20 using control board 400 of FIG. 11 illustrates there is very little difference in the output of the sensor when the conductivity changes from zero to 3.26 mS/cm, to 7.45 mS/cm, to 10.38 mS/cm, to 12.38 mS/cm and to 15.13 mS/cm. It is also expected that the conductivity could be increased past fifteen mS/cm without significantly affecting sensor output using the phase shift methodology. When using control board 400 in system 10, conductivity does not come into play, such that the tuning electronics described above are not needed.

The curve of FIG. 12 flattens out at fill levels 4 to 6, which is due to the particular structure of transmission lines or electrodes 24 and 26 used for the experiment. If needed, the curve can be corrected by changing the physical structure of one or both of electrodes 24 and 26. Or, like described above for system 10, it may be sufficient to operate with the changing or diagonal parts of the curve only, here for example, if only the bottom region (empty) and the top region (full) of tank 40 are of interest for the particular application.

As described above, advantages of system 10 include that it requires relatively simple packaging and implementation, is non-invasive, is tolerant to high temperature (e.g., 100° C.) and humidity (e.g., 100%), is relatively low cost, provides good resolution and repeatability, provides continuous, real-time monitoring, and should require relatively low maintenance.

When the circuit of FIG. 11 is implemented to determine tank level, the calibration process correlates each phase reading with a tank level. In one embodiment, the operating frequency of the system is chosen during calibration such that the entire range of possible fluid levels and associated phase shifts falls into a linear portion of the sinusoidal wave describing the phase of the overall impedance of the tank.

Figure 13:
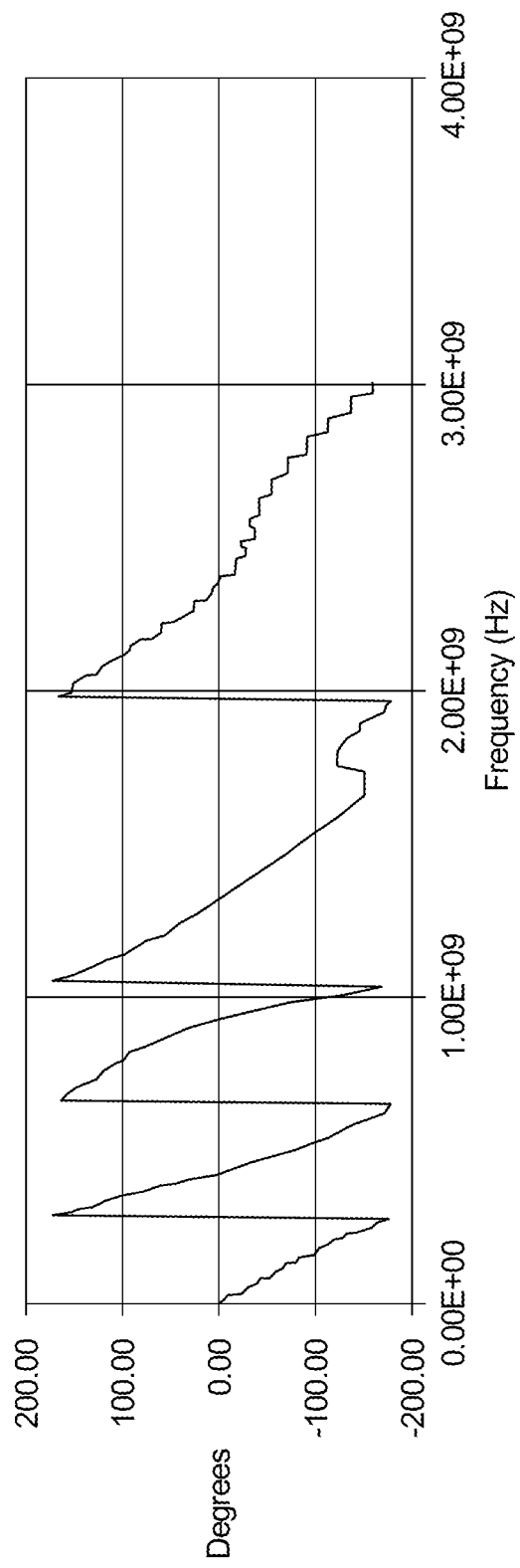
FIG. 13 is a graph of a frequency sweep performed when the tank is empty.
Figure 14:
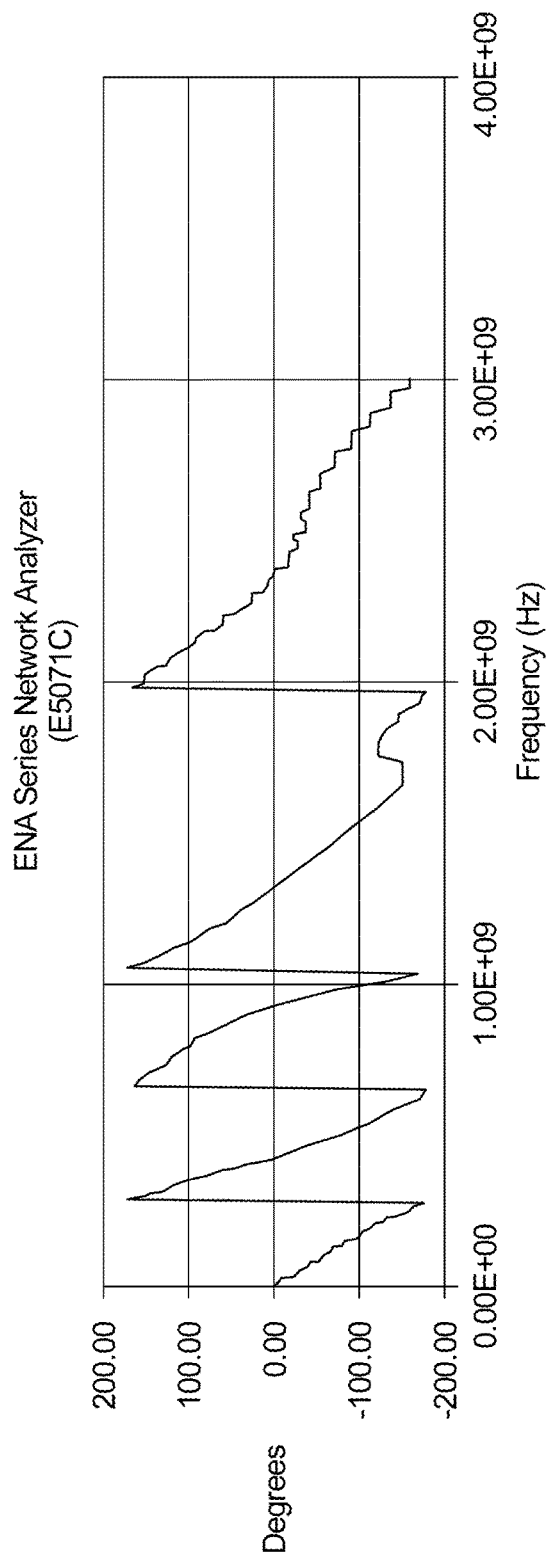
FIG. 14 is a graph of a frequency sweep performed when the tank is full.
Figure 15:
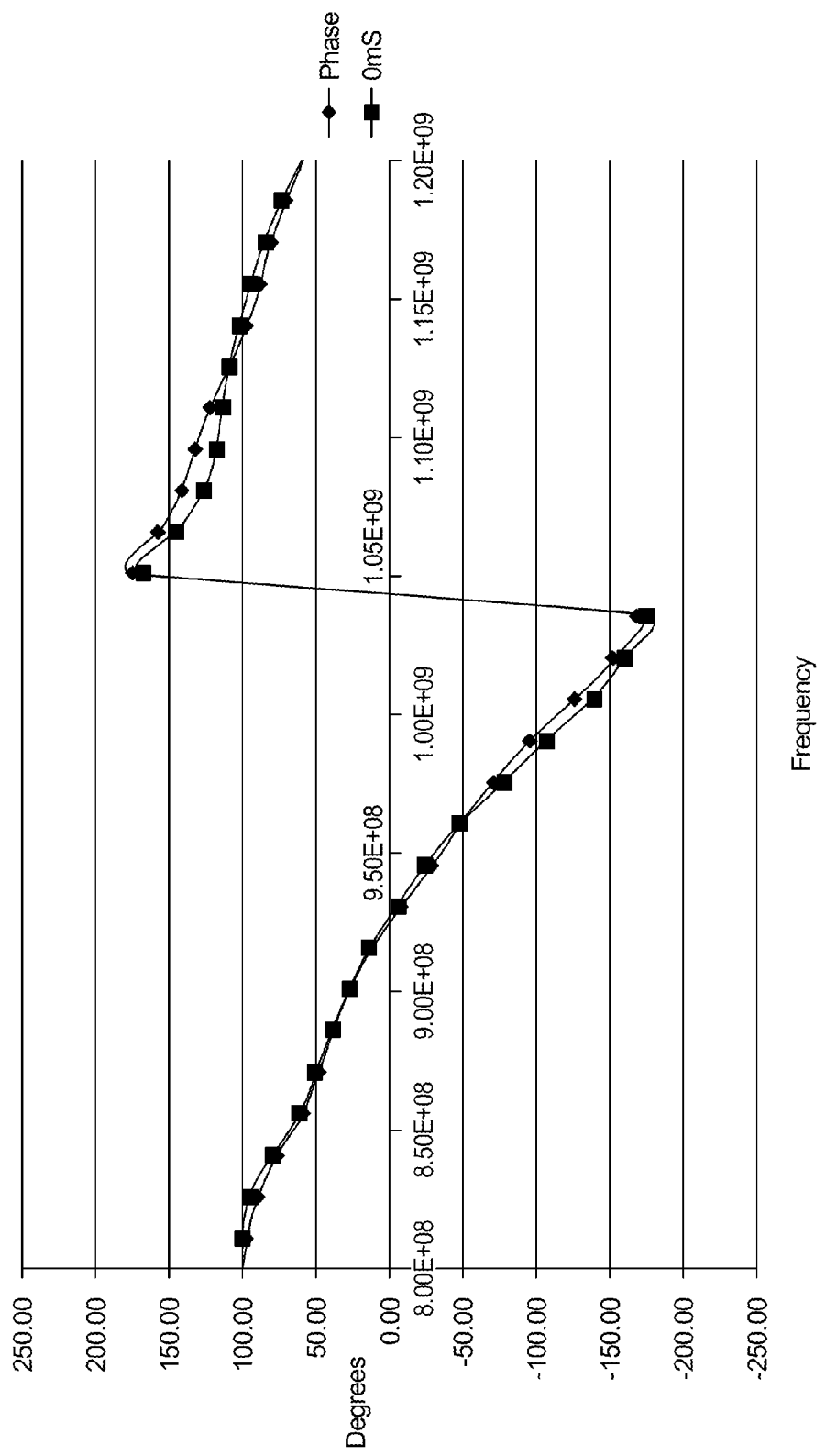
FIG. 15 is a graph of the frequency sweeps of FIGS. 13 and 15 plotted together to determine an operating frequency.

FIGS. 13 and 14 illustrate example frequency sweeps used to select an operating frequency. The entire frequency range is swept when the tank is empty and the phase shift of the signal in the transmission line is read, as shown in FIG. 13. Then, the entire frequency range is swept when the tank is full of water, e.g., reverse osmosis water, and the phase shift of the signal in the transmission line is read, as shown in FIG. 14. The graphs resulting from the two sweeps are plotted together, as shown in FIG. 15, and the two graphs are analyzed for a frequency where the two graphs substantially overlap each other. In the example plot of FIG. 15, the two graphs substantially overlap at 1.4 GHz, and thus setting 1.4 GHz as the frequency of the VCO ensures that the phase of the sensor remains substantially linear for all possible tank levels ranging from empty to full. This ensures that each reading of the phase corresponds to a unique medical fluid level, enhancing the accuracy and reliability of the system.

Figure 16:
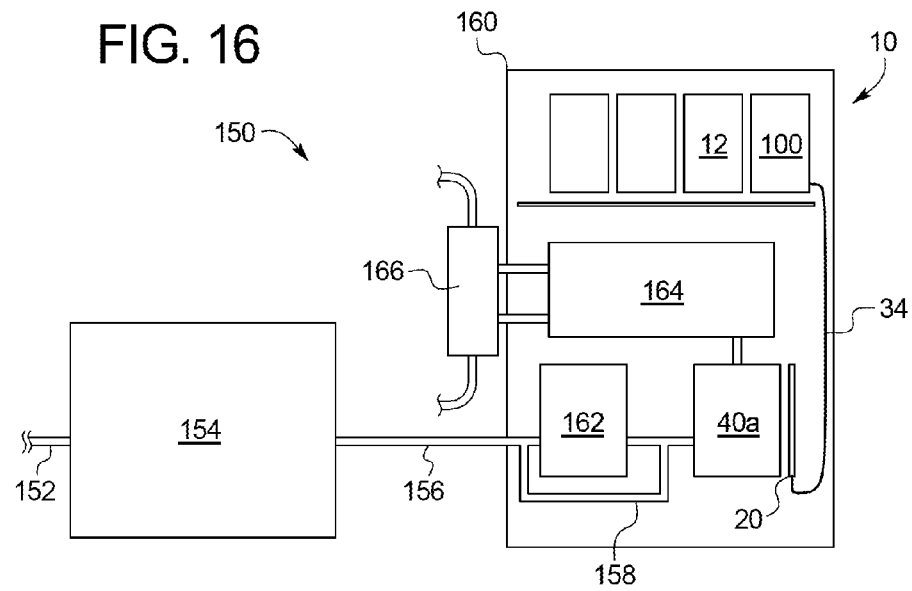
FIG. 16 is a schematic diagram illustrating any of the tank or container level or volume sensors discussed herein operating with an online blood therapy treatment system.

Referring now to FIGS. 16 to 19, different medical systems employing system 10 are illustrated. FIG. 16 illustrates an online hemodialysis system 150 employing the level or volume detection system 10. Online hemodialysis system 150 pulls water via line 152 from a house or tap supply of water. Line 152 leads to an online water purification system 154, which purifies the water to make the water suitable for a dialysis therapy. Filtered water is delivered via line 156 to a hemodialysis machine 160. Filtered water line 156 enters dialysis machine 160 and feeds a dialysis preparation unit 162, which includes pumps, valves, lines and chemicals needed to create online dialysate from filtered water traveling through line 156. One suitable dialysis machine 160 having a dialysis generation unit 162 is described in U.S. Publication No. 2009/0008331, entitled "Hemodialysis Systems and Methods", filed Feb. 27, 2008, the entire contents of which are hereby incorporated by reference, for environmental purposes related to system 10 and sensor 20, which are otherwise fully and completely described herein.

Dialysis machine 160 also includes a bypass 158, which allows purified water to be delivered to dialysate preparation unit 162. A storage container or tank 40a of dialysis machine 160 can at different times store a level and volume of dialysate emanating from preparation unit 162 or store a level and volume of purified water via bypass line 158. Dialysis machine 160 uses the mixed dialysate for therapy purposes. Dialysis machine 160 uses the purified water instead for flushing, priming, rinsing, recirculation and disinfection when therapy is not occurring dialysate is not needed.

Dialysate or purified water is delivered to a dialysate therapy unit 164, which heats and delivers dialysate in a controlled and desired manner to a dialyzer 166. In the illustrated embodiment, system 150 uses liquid level and volume detection system 10 having sensor 20 placed adjacent or onto storage vessel 40a. Cable or ribbon 34 extends from sensor 20 to a safe processing area within the enclosure of dialysis machine 160 and to a control board 100 for example. Control board 100 communicates with a processing board 12 in the embodiment shown in FIG. 16.

Figure 17:
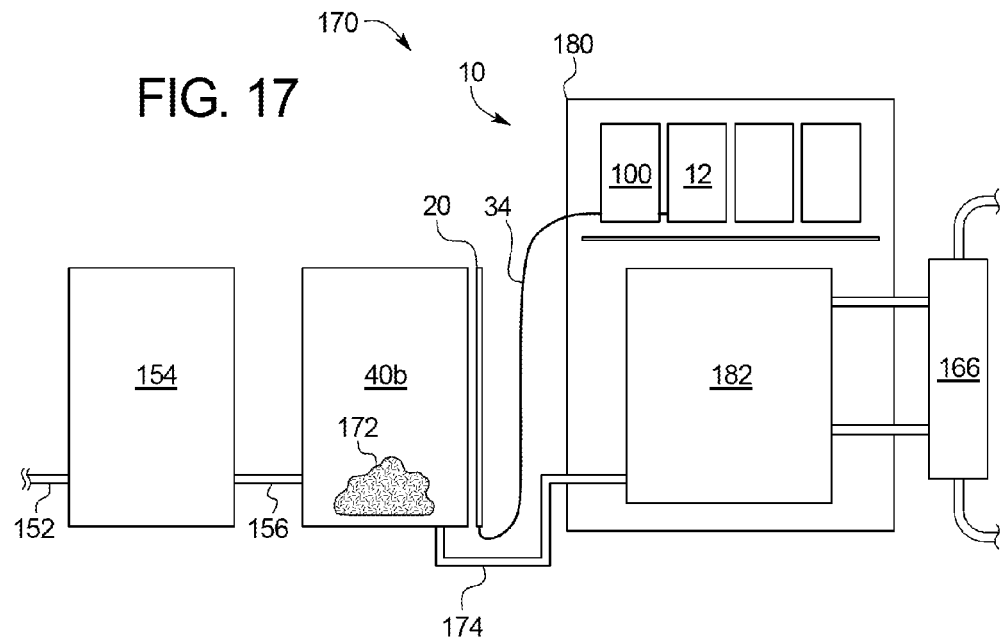
FIG. 17 is a schematic diagram illustrating any of the tank or container level or volume sensors discussed herein operating with a batch or semi-batch blood therapy treatment system.

Referring now to FIG. 17, a batch or semi-batch hemodialysis system 170 is illustrated. One example batch or semi-batch dialysis system is described in U.S. Pat. No. 7,749,393, entitled "Batch Filtration System For Preparation Of Sterile Fluid For Renal Replacement Therapy", filed May 1, 2009, the entire contents of which are incorporated herein by reference for environmental purposes related to system 10 and sensor 20, which are otherwise fully and completely described herein. Dialysis system 170, like dialysis system 150, includes a water inlet line 152 leading to online water purification unit 154 as described above. Filtered water leaves purification unit 154 via purified water line 156 but is delivered instead to tank or container 40b, which holds a supply of chemicals 172 needed to convert purified water via line 156 into dialysate suitable for use in a dialysis machine 180. Sensor 20 is connected via cable or ribbon 34 to control card 100, which in turn communicates with microprocessor and associated memory 12 as has been described herein.

Dialysis machine 180 pulls mixed dialysate from tank or container 40b via dialysate inlet line 174. Dialysate inlet line 174 leads to a dialysate heating and volume control delivery unit 182. Dialysate delivery unit 182 delivers heated dialysate in a controlled manner (pressure and flow) to dialyzer 166 and likewise removes dialysate from dialyzer 166 in a like controlled manner, for example, removing a desired amount of utrafiltration from the patient.

Sensing system 10 is provided here to detect the level of purified water from unit 154 that has been filled within tank or container 40b. Sensor 20 measures the fluid level rising initially to a point at which it is known that the concentrate chemicals 172 have been diluted to a sufficient level for use for therapy.

This level can be confirmed if needed via one or more temperature compensated conductivity readings. Level sensor 20 and sensing system 10 are then used during therapy, and perhaps over multiple therapies if enough batch dialysate has been made, to determine how much mixed dialysate remains within container 40b. It is contemplated for example that if sensing system 10 indicates that not enough dialysate is left within batch container 40b for an ongoing or new therapy, the patient is notified accordingly.

Figure 18:
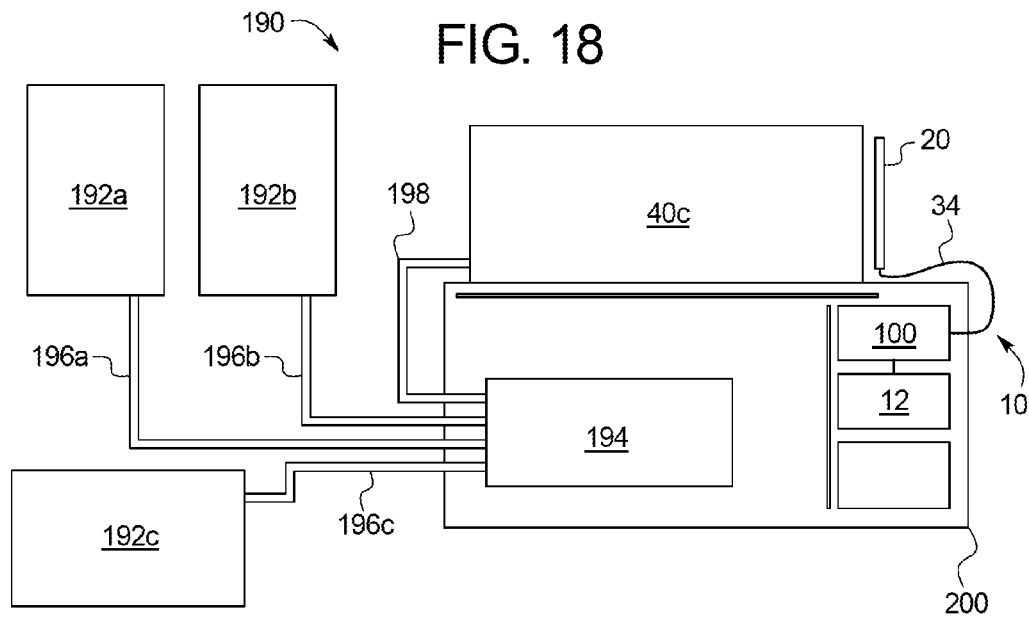
FIG. 18 is a schematic diagram illustrating any of the tank or container level or volume sensors discussed herein operating with bagged peritoneal dialysis system.

Referring now to FIG. 18, system 10 is illustrated in operation with a bagged peritoneal dialysis system 190. One suitable peritoneal dialysis system 190 is described in Patent Cooperation Treaty ("PCT") Publication No. WO 2009/094183, entitled "Fluid Line Autoconnect Apparatus And Methods For Medical Treatment System", filed Jan. 23, 2009 (in PCT), the entire contents which are incorporated herein by reference for environmental purposes related to system 10 and sensor 20, which are otherwise fully and completely described herein.

Peritoneal dialysis system 190 includes a plurality of supply bags 192a to 192c of premixed dialysate that is suitable for injection into the patient's peritoneum. Each of supply bags 192a to 192c is preconnected to a dialysate pumping cassette 194 via supply lines 196a to 196c, respectively. A peritoneal dialysis cycler 200 is provided to operate pumping and valving cassette 194. In particular, cycler 200 pulls fluid from one of supply bags 192a to 192c and delivers that fluid via heater line 198 to a dialysate heating vessel 40c. When the fluid within heating vessel 40c is heated to a desired level, cycler 200 pulls heated dialysate back from heater line 198 into cassette 194 and then out to the patient.

Sensing system 10 uses sensor 20 as described herein to determine how much fluid has been delivered to and removed from dialysate heating container 40c. In the illustrated embodiment, sensor 20 communicates with control board 100 via electrical lines within cable or ribbon 34. Control board 100 in turn communicates via processing unit 12.

It should be appreciated that while premixed dialysate is used in one embodiment, it is also expressly contemplated to pull (i) dialysate constituents from different bags 192a to 192c or (ii) premixed dialysates having different dextrose or glucose levels from the different bags to produce and mix the constituents or the different dialysates within heating/mixing container 40c. Sensing system 10 is used to know how much of each constituent or dialysate has been pumped from any of the bags 192a to 192c into container 40c. For example, premixed dialysates having different dextrose or glucose levels can be pulled in desired amounts from bags 192a to 192c to produce a desired hybrid dialysate within mixing container 40c, which is then heated for delivery to the patient. Or, peritoneal dialysis constituents that are not stable if premixed can be pulled from separate bags.

Figure 19:
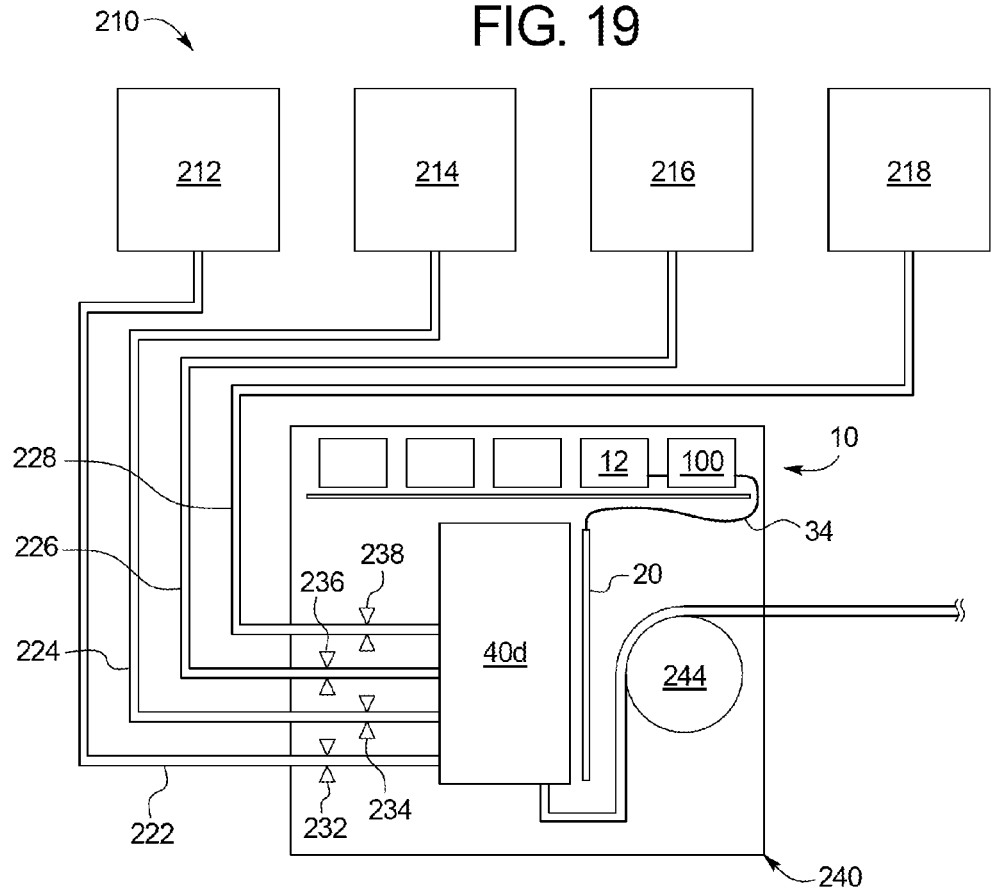
FIG. 19 is a schematic diagram illustrating any of the tank or container level or volume sensors discussed herein operating with medical fluid mixing system.

Referring now to FIG. 19, dialysate sensing system 10 is used with a medical fluid delivery system 210, which can deliver one or more drugs via drug containers 212, 214, 216 and 218 intravenously to the patient via a drug infusion pump 240. One suitable embodiment for drug infusion pump 240 is described in U.S. Pat. No. 6,269,340, filed Oct. 27, 1997, entitled "Infusion Pump With An Electronically Loadable Drug Library And A User Interface For Loading The Library", the entire contents of which are incorporated herein by reference for environmental purposes related to system 10 and sensor 20, which are otherwise fully and completely described herein. The different drugs are selectively pumped to a drug holding tank 40d via fluid lines 222, 224, 226 and 228, respectively. The infusion pump selectively pumps from the drug supplies via the opening and closing of valves 232, 234, 236 and 238, respectively. A pump such as a peristaltic pump 244 of infusion pump 240 pumps a drug or mixture thereof from holding tank 40d to the patient.

Similar to the peritoneal dialysis system 190 of FIG. 18, the drug delivery system 210 of FIG. 19 can deliver drugs sequentially from supplies 212 to 218 through drug holding tank 40d to the patient. Alternately, drug constituents or premixed drugs are mixed within container 40d. Sensor 20 monitors the total amount of fluid within holding tank 40d. Sensor 20 also meters in precise amounts of drugs from any of supplies 212 to 218 in combination to arrive at a desired drug or drug mixture within container 40d. Sensing system 10 includes sensor 20 connected to control board 100 via cable or ribbon 34. Control board 100 in turn communicates with processing unit 12.

Aspects of the subject matter described herein may be useful alone or in combination one or more other aspect described herein. Without limiting the foregoing description, in a first aspect of the present disclosure, a medical fluid system includes a container holding a fluid, the fluid at a first time having a first conductivity, the fluid at a second time having a second conductivity; and a radio frequency level sensor positioned in operable relation with the container, the radio frequency operation of the level sensor configured to be (i) indicative of a level or volume of the fluid in the container and (ii) at least substantially independent of whether the fluid has the first conductivity or the second conductivity.

In accordance with a second aspect of the present disclosure, which may be used in combination with the first aspect, the system is a dialysis system, and wherein the container is a (a) dialysate supply container or (b) a dialysate holding container in fluid communication with a supply of dialysate.

In accordance with a third aspect of the present disclosure, which may be used in combination with any one or more of the preceding aspects, the system is a dialysis system, the fluid being water at the first time and dialysate at the second time.

In accordance with a fourth aspect of the present disclosure, which may be used in combination with any one or more of the preceding aspects, the system is an intravenous drug infusion system, the container at the first time holding a first drug at the first conductivity and at the second time holding a second drug at the second conductivity.

In accordance with a fifth aspect of the present disclosure, which may be used in combination with any one or more of the preceding aspects, the container is reusable.

In accordance with a sixth aspect of the present disclosure, which may be used in combination with any one or more of the preceding aspects, the radio frequency level sensor is fixed to the container.

In accordance with a seventh aspect of the present disclosure, which may be used in combination with any one or more of the preceding aspects, the radio frequency level sensor is spaced apart from the container.

In accordance with an eighth aspect of the present disclosure, which may be used in combination with any one or more of the preceding aspects, the medical fluid system is configured and arranged to mix different constituents of the fluid resulting in the first and second conductivities at the first and second times.

In accordance with a ninth aspect of the present disclosure, which may be used in combination with any one or more of the preceding aspects, the radio frequency level sensor includes a radio frequency signal emitting electrode spaced adjacent to a radio frequency signal receiving electrode.

In accordance with a tenth aspect of the present disclosure, which may be used in combination with the ninth aspect, the emitting and receiving electrodes extend a length indicative of a full level of the fluid holding container.

In accordance with an eleventh aspect of the present disclosure, which may be used in combination with the ninth aspect, the emitting electrode is spaced adjacent to the receiving electrode so as to form a characteristic impedance.

In accordance with a twelfth aspect of the present disclosure, which may be used in combination with the ninth aspect, the emitting electrode and the receiving electrode are at least one of: (i) sized so as to form a characteristic impedance and (ii) sized the same.

In accordance with a thirteenth aspect of the present disclosure, which may be used in combination with any one or more of the preceding aspects, the system includes a processor operable with the level sensor, the sensor outputting a signal indicative of a fluid level effected impedance to the processor.

In accordance with a fourteenth aspect of the present disclosure, which may be used in combination with the thirteenth aspect, the system includes at least one converter operating between the sensor and the processor, the converter converting the signal into a form suitable for the processor.

In accordance with a fifteenth aspect of the present disclosure, which may be used in combination with the thirteenth aspect, the processor is configured to provide a radio frequency input to the sensor.

In accordance with a sixteenth aspect of the present disclosure, which may be used in combination with the thirteenth aspect, the processor is configured to operate with stored data relating the signal or a variant thereof to one of (i) the level of the fluid in the container or (ii) the volume of the fluid in the container.

In accordance with a seventeenth aspect of the present disclosure, which may be used in combination with any one or more of the preceding aspects, a medical fluid system includes a medical fluid pump; a container in fluid communication with a medical fluid pump, the container at a first time holding a first fluid having a first conductivity, the container at a second time holding a second fluid having a second conductivity; and a radio frequency level sensor positioned in operable relation with the container, the radio frequency operation of the level sensor configured so as to be (i) indicative of a level or volume of the first or second fluid in the container and (ii) at least substantially independent of the first and second conductivities.

In accordance with an eighteenth aspect of the present disclosure, which may be used in with any one or more of the preceding aspects in combination with the seventeenth aspect, the system is a dialysis system, the first fluid being water and the second fluid being dialysate.

In accordance with a nineteenth aspect of the present disclosure, which may be used in with any one or more of the preceding aspects in combination with the seventeenth aspect, the system is an intravenous drug infusion system, the first fluid being a first drug and the second fluid being a second drug.

In accordance with a twentieth aspect of the present disclosure, which may be used in with any one or more of the preceding aspects in combination with the seventeenth aspect, the system is an intravenous drug infusion system, the first fluid being a first drug constituent and the second fluid being a second drug constituent.

In accordance with a twenty-first aspect of the present disclosure, which may be used in with any one or more of the preceding aspects in combination with the seventeenth aspect, the system is a peritoneal dialysis system, the first fluid being a first peritoneal dialysate and the second fluid being a second peritoneal dialysate.

In accordance with a twenty-second aspect of the present disclosure, which may be used in with any one or more of the preceding aspects in combination with the seventeenth aspect, the system is a peritoneal dialysis system, the first fluid being a first peritoneal dialysis fluid constituent and the second fluid being a second peritoneal dialysis constituent.

In accordance with a twenty-third aspect of the present disclosure, which may be used in combination with any one or more of the preceding aspects, a medical fluid system includes a medical fluid pump; a container holding a fluid to be pumped by the medical fluid pump; and a radio frequency sensor operable with the container, the sensor including an emitting electrode and a receiving electrode positioned such that a radio frequency transmission between the emitting electrode and the receiving electrode is affected by an amount of air in the container having a dielectric constant $\varepsilon_o$ and an amount of fluid in the container having a dielectric constant $\varepsilon_d$, the container at a first time holding a first fluid and at a second time holding a second fluid having a different conductivity then the first fluid, the first and second fluids having at least substantially the same dielectric constant $\varepsilon_d$, the sensor outputting an impedance signal indicative of an equivalent dielectric constant $\varepsilon$, the equivalent dielectric constant $\varepsilon$ based on the dielectric constants $\varepsilon_o$ and $\varepsilon_d$.

In accordance with a twenty-fourth aspect of the present disclosure, which may be used in with any one or more of the preceding aspects in combination with the twenty-third aspect, the equivalent dielectric constant $$\varepsilon = \frac{\varepsilon o + \varepsilon d}{2}.$$

In accordance with a twenty-fifth aspect of the present disclosure, which may be used in with any one or more of the preceding aspects in combination with the twenty-third aspect, the value of the fluid dielectric constant $\varepsilon_d$ varies based on a level of the fluid.

In accordance with a twenty-sixth aspect of the present disclosure, which may be used in combination with any one or more of the preceding aspects, a medical fluid method includes pumping a first fluid having a first conductivity from a container; pumping a second fluid having a second different conductivity from the container; and sensing a level or volume of the first and second fluids using a radio frequency transmission that is independent of fluid conductivity.

In accordance with a twenty-seventh aspect of the present disclosure, any of the structure and functionality illustrated and described in connection with FIG. 1 may be used in combination with any one or more of the preceding aspects.

In accordance with a twenty-eighth aspect of the present disclosure, any of the structure and functionality illustrated and described in connection with FIG. 2 may be used in combination with any one or more of the preceding aspects.

In accordance with a twenty-ninth aspect of the present disclosure, any of the structure and functionality illustrated and described in connection with FIG. 3 may be used in combination with any one or more of the preceding aspects.

In accordance with a thirtieth aspect of the present disclosure, any of the structure and functionality illustrated and described in connection with FIG. 4 may be used in combination with any one or more of the preceding aspects.

In accordance with a thirty-first aspect of the present disclosure, any of the structure and functionality illustrated and described in connection with FIG. 5 may be used in combination with any one or more of the preceding aspects.

In accordance with a thirty-second aspect of the present disclosure, any of the structure and functionality illustrated and described in connection with FIG. 6 may be used in combination with any one or more of the preceding aspects.

In accordance with a thirty-third aspect of the present disclosure, any of the structure and functionality illustrated and described in connection with FIG. 7 may be used in combination with any one or more of the preceding aspects.

In accordance with a thirty-fourth aspect of the present disclosure, any of the structure and functionality illustrated and described in connection with FIG. 8 may be used in combination with any one or more of the preceding aspects.

In accordance with a thirty-fifth aspect of the present disclosure, any of the structure and functionality illustrated and described in connection with FIG. 9 may be used in combination with any one or more of the preceding aspects.

In accordance with a thirty-sixth aspect of the present disclosure, any of the structure and functionality illustrated and described in connection with FIG. 10 may be used in combination with any one or more of the preceding aspects.

In accordance with a thirty-seventh aspect of the present disclosure, any of the structure and functionality illustrated and described in connection with FIG. 11 may be used in combination with any one or more of the preceding aspects.

In accordance with a thirty-eighth aspect of the present disclosure, any of the structure and functionality illustrated and described in connection with FIG. 12 may be used in combination with any one or more of the preceding aspects.

In accordance with a thirty-ninth aspect of the present disclosure, any of the structure and functionality illustrated and described in connection with FIG. 13 may be used in combination with any one or more of the preceding aspects.

In accordance with a fortieth aspect of the present disclosure, any of the structure and functionality illustrated and described in connection with FIG. 14 may be used in combination with any one or more of the preceding aspects.

In accordance with a forty-first aspect of the present disclosure, any of the structure and functionality illustrated and described in connection with FIG. 15 may be used in combination with any one or more of the preceding aspects.

In accordance with a forty-second aspect of the present disclosure, any of the structure and functionality illustrated and described in connection with FIG. 16 may be used in combination with any one or more of the preceding aspects.

In accordance with a forty-third aspect of the present disclosure, any of the structure and functionality illustrated and described in connection with FIG. 17 may be used in combination with any one or more of the preceding aspects.

In accordance with a forty-fourth aspect of the present disclosure, any of the structure and functionality illustrated and described in connection with FIG. 18 may be used in combination with any one or more of the preceding aspects.

In accordance with a forty-fifth aspect of the present disclosure, any of the structure and functionality illustrated and described in connection with FIG. 19 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid system comprising:
a container holding a fluid, the fluid at a first time having a first conductivity, the fluid at a second time having a second conductivity; and
a radio frequency level sensor positioned in operable relation with the container, the radio frequency level sensor (i) configured to provide an output indicative of a level or a volume of the fluid in the container based upon sensing an impedance that varies with the level or the volume of the fluid in the container and (ii) connected to tuning circuitry including a plurality of components tuned to an operating frequency to minimize a reactance of the impedance at the operating frequency such that the output is at least substantially independent of whether the fluid has the first conductivity or the second conductivity.

2. The medical fluid system of claim 1, which is a dialysis system, and wherein the container is (i) a dialysate supply container or (ii) a dialysate holding container in fluid communication with a supply of dialysate.

3. The medical fluid system of claim 1, which is a dialysis system, the fluid being water at the first time and dialysate at the second time.

4. The medical fluid system of claim 1, wherein the radio frequency level sensor is fixed to the container.

5. The medical fluid system of claim 1, wherein the radio frequency level sensor is spaced apart from the container.

6. The medical fluid system of claim 1, which is configured and arranged to mix different constituents of the fluid resulting in the first and second conductivities at the first and second times.

7. The medical fluid system of claim 1, wherein the radio frequency level sensor includes a radio frequency signal emitting electrode spaced adjacent to a radio frequency signal receiving electrode.

8. The medical fluid system of claim 7, wherein the emitting electrode and the receiving electrode are at least one of: (i) sized so as to form a characteristic impedance and (ii) sized the same.

9. The medical fluid system of claim 1, which includes a processor operable with the level sensor, the sensor outputting a signal indicative of the impedance to the processor.

10. The medical fluid system of claim 9, wherein the processor is configured to provide a radio frequency input to the sensor.

11. The medical fluid system of claim 9, wherein the processor is configured to operate with stored data relating the signal or a variant thereof to one of (i) the level of the fluid in the container or (ii) the volume of the fluid in the container.

12. The medical fluid system of claim 1, wherein each of the plurality of components is tuned during a calibration.

13. The medical fluid system of claim 1, wherein the plurality of components includes at least one capacitor and at least one inductor.

14. The medical fluid system of claim 1, wherein the reactance is driven to zero at the operating frequency by the tuning circuitry.

15. The medical fluid system of claim 1, wherein the operating frequency is in a range from 1 GHz to 2 GHz.

16. The medical fluid system of claim 1, wherein each component of the plurality of components has (i) a first respective value that drives the reactance to zero at a first operating frequency, and (ii) a second respective value that drives the reactance to zero at a second, different operating frequency.

17. The medical fluid system of claim 1, which includes an oscillator configured to generate a radio frequency signal at the operating frequency.

18. A medical fluid system comprising:
a medical fluid pump;
a container in fluid communication with the medical fluid pump, the container at a first time holding a first fluid having a first conductivity, the container at a second time holding a second fluid having a second conductivity; and
a radio frequency level sensor positioned in operable relation with the container, the radio frequency level sensor (i) configured to provide an output indicative of a level or a volume of the first or second fluid in the container based upon sensing an impedance that varies with the level or the volume of the first or second fluid in the container and (ii) connected to tuning circuitry including a plurality of components tuned to an operating frequency to minimize a reactance of the impedance at the operating frequency such that the output is at least substantially independent of the first and second conductivities.

19. The medical fluid system of claim 18, which is a dialysis system, the first fluid being water and the second fluid being dialysate.

20. The medical fluid system of claim 18, which is an intravenous drug infusion system, the first fluid being a first drug and the second fluid being a second drug.

21. The medical fluid system of claim 18, which is an intravenous drug infusion system, the first fluid being a first drug constituent and the second fluid being a second drug constituent.

22. The medical fluid system of claim 18, which is a peritoneal dialysis system, the first fluid being a first peritoneal dialysate and the second fluid being a second peritoneal dialysate.

23. The medical fluid system of claim 18, which is a peritoneal dialysis system, the first fluid being a first peritoneal dialysis fluid constituent and the second fluid being a second peritoneal dialysis constituent.

24. A medical fluid system comprising:
a medical fluid pump;
a container holding a fluid to be pumped by the medical fluid pump; and
a radio frequency sensor operable with the container, the sensor including an emitting electrode and a receiving electrode positioned such that a radio frequency transmission between the emitting electrode and the receiving electrode is affected by an amount of air in the container having a dielectric constant $\in_o$ and an amount of the fluid in the container having a dielectric constant $\in_d$, the container at a first time holding a first fluid and at a second time holding a second fluid having a different conductivity than the first fluid, the first and second fluids having at least substantially the same dielectric constant $\in_d$, the sensor outputting an impedance signal indicative of an equivalent dielectric constant E, which is indicative of a fluid level of the container, the equivalent dielectric constant E based on the dielectric constants $\in_o$ and $\in_d$, and the sensor connected to tuning circuitry including a plurality of components tuned to an operating frequency to minimize a reactance of an impedance at the operating frequency such that the impedance signal is at least substantially independent of the conductivities of the first and second fluids.

25. The system of claim 24, wherein the equivalent dielectric constant is $$\varepsilon = \frac{\varepsilon o + \varepsilon d}{2}.$$

26. The system of claim 24, wherein a value of the dielectric constant $\in_d$ varies based on the fluid level.

* * * * *